US012751631B2

(12) United States Patent
Herrera Soukup et al.

(10) Patent No.: US 12,751,631 B2
(45) Date of Patent: Oct. 6, 2026

(54) PHOTOACOUSTIC SENSOR USING MICROMACHINED ULTRASONIC TRANSDUCERS

(71) Applicant: QUALCOMM Incorporated, San Diego, CA (US)

(72) Inventors: Bernard Herrera Soukup, Sunnyvale, CA (US); Hrishikesh Vijaykumar Panchawagh, Cupertino, CA (US); Sumit Agrawal, Sunnyvale, CA (US); Nicholas Buchan, San Jose, CA (US); John Keith Schneider, Williamsville, NY (US); Kostadin Dimitrov Djordjev, Los Gatos, CA (US)

(73) Assignee: QUALCOMM Incorporated, San Diego, CA (US)

( * ) Notice: Subject to any disclaimer, the term of this patent is extended or adjusted under 35 U.S.C. 154(b) by 127 days.

(21) Appl. No.: 18/608,619

(22) Filed: Mar. 18, 2024

(65) Prior Publication Data

US 2025/0288209 A1 Sep. 18, 2025

(51) Int. Cl.

| | |
|---|---|
| ***A61B 5/00*** | (2006.01) |
| ***A61B 8/00*** | (2006.01) |
| ***A61B 8/08*** | (2006.01) |
| ***H10N 30/85*** | (2023.01) |
| ***H10N 30/88*** | (2023.01) |

(52) U.S. Cl.

CPC .......... *A61B 5/0095* (2013.01); *A61B 5/0037* (2013.01); *A61B 8/0891* (2013.01); *A61B 8/4477* (2013.01); *A61B 8/4494* (2013.01); *H10N 30/852* (2023.02); *H10N 30/883* (2023.02)

(58) Field of Classification Search

CPC ... A61B 5/0095; A61B 5/0037; A61B 8/0891; A61B 8/4477; A61B 8/4494; H10N 30/852; H10N 30/883

See application file for complete search history.

(56) References Cited

U.S. PATENT DOCUMENTS

| | | | | |
|---|---|---|---|---|
| 2011/0026367 | A1 * | 2/2011 | Noelle | B06B 1/02 367/189 |
| 2017/0231598 | A1 * | 8/2017 | Baek | A61B 8/54 600/454 |
| 2020/0410189 | A1 * | 12/2020 | Kitchens | G06F 21/32 |
| 2022/0175258 | A1 * | 6/2022 | Kitchens | A61B 5/02116 |
| 2023/0042741 | A1 * | 2/2023 | Rohling | G01N 29/2406 |

FOREIGN PATENT DOCUMENTS

| | | | | |
|---|---|---|---|---|
| WO | WO-2025114210 A1 * | 6/2025 | | A61B 8/4444 |

* cited by examiner

*Primary Examiner* — Andrew W Begeman

(74) *Attorney, Agent, or Firm* — QUALCOMM Incorporated

(57) ABSTRACT

Some disclosed examples pertain to a photoacoustic apparatus that can include a substrate such as a semiconductor substrate, a light source system that includes one or more light-emitting elements on the substrate, and an ultrasonic receiver system that includes an array of micromachined ultrasonic transducer elements on the substrate. The ultrasonic receiver system is configured to detect acoustic waves corresponding to a photoacoustic response of a target object to light provided by the light source system. In some implementations, the photoacoustic apparatus includes an encapsulation layer disposed over the light source system and the ultrasonic receiver system.

16 Claims, 13 Drawing Sheets

PHOTOACOUSTIC SENSOR USING MICROMACHINED ULTRASONIC TRANSDUCERS

TECHNICAL FIELD

This disclosure relates generally to photoacoustic devices and more specifically to compact photoacoustic devices.

DESCRIPTION OF RELATED TECHNOLOGY

A variety of different sensing technologies and algorithms are being implemented in devices for various biometric and biomedical applications, including health and wellness monitoring. This push is partly a result of the limitations in the usability of traditional measuring devices for continuous, noninvasive and ambulatory monitoring. Some such devices are, or include, photoacoustic devices. Although some existing photoacoustic devices may be relatively effective, photoacoustic devices having improved features and improved performance would be desirable.

SUMMARY

The systems, methods, and devices of this disclosure each have several aspects, no single one of which is solely responsible for the desirable attributes disclosed herein.

One innovative aspect of the subject matter described in this disclosure can be implemented in an apparatus that includes a substrate, a light source system formed on the substrate and configured to provide light to a target object, an ultrasonic receiver system formed on the substrate and comprising an array of ultrasonic transducer elements, and an encapsulation layer disposed over the array of ultrasonic transducer elements and the light source system. The ultrasonic receiver system is configured to detect acoustic waves corresponding to a photoacoustic response of the target object to light provided by the light source system. The encapsulation layer is transparent to the light provided by the light source system.

In some implementations, the array of ultrasonic transducer elements comprises an array of piezoelectric micromachined ultrasonic transducers (PMUTs). In some implementations, the array of PMUTs are configured to operate at different resonant frequencies. In some implementations, each of the PMUTs comprises a piezoelectric layer sandwiched between a top electrode and a bottom electrode disposed on a supporting silicon substrate. A material of the piezoelectric layer is selected from a group consisting of: aluminum nitride (AlN), aluminum scandium nitride (AlScN), lead zirconate titanate (PZT), lithium niobate, zinc oxide, and co-polymer. In some implementations, the array of PMUTs are transparent to the light provided by the light source system. In some implementations, the light source system and the ultrasonic receiver system are integrated in an integrated receiver/transmitter chip, where the array of PMUTs is interleaved between a plurality of light-emitting elements in the light source system. In some implementations, the array of ultrasonic transducer elements comprises an array of capacitive micromachined ultrasonic transducers (CMUTs). In some implementations, the apparatus further comprises a control system formed on the substrate. The control system comprises one or more processors and one or more memory devices, where the control system is in electrical communication with the ultrasonic receiver system and the light source system. In some implementations, the substrate comprises a printed circuit board or flexible circuit board on which each of the light source system, ultrasonic receiver system, and control system is formed. In some implementations, the control system is further configured with instructions to perform the following operations: process ultrasonic receiver signals from the ultrasonic receiver system, amplify the ultrasonic receiver signals, produce a beamformed ultrasonic receiver image, and detect a blood vessel within the target object based at least in part on the beamformed ultrasonic receiver image. In some implementations, the control system is further configured with instructions to perform the following operation: estimate one or more cardiac features based, at least in part, on the blood vessel within the target object. In some implementations, a thickness of the apparatus comprising the encapsulation layer, the substrate, the ultrasonic receiver system, and the light source system is equal to or less than about 4 mm. In some implementations, the light source system includes one or more vertical cavity surface emitting laser (VCSEL) chips. In some implementations, the light source system includes one or more edge-emitting laser (EEL) chips. In some implementations, the apparatus further includes: a plurality of light guides to route light from the one or more EEL chips to multiple areas located on a plane of the substrate, and a plurality of diffraction gratings optically coupled to the plurality of light guides and configured to direct light from each of the multiple areas to the target object. In some implementations, an acoustic impedance of the encapsulation layer matches or substantially matches an acoustic impedance of human skin.

Other innovative aspects of the subject matter described in this disclosure can be implemented in an apparatus for estimating one or more cardiac features, where the apparatus includes a substrate, a light source system comprising a plurality of light-emitting elements formed on the substrate, an ultrasonic receiver system comprising an array of piezoelectric micromachined ultrasonic transducers (PMUTs) formed on the substrate, and a control system formed on the substrate. The apparatus further includes an encapsulation layer disposed over the plurality of light-emitting elements, the array of PMUTs, and the control system. The control system is configured with instructions to perform the following operations: cause the light source system to emit light towards human tissue in contact with an outer surface of the encapsulation layer, receive ultrasonic signals from each of the PMUTs in the ultrasonic receiver system corresponding to ultrasonic waves generated by the human tissue, identify one or more blood vessels, and estimate one or more cardiac features based, at least in part, on the one or more blood vessels.

In some implementations, the control system is further configured with instructions for performing the following operations: amplify the ultrasonic signals received from each of the PMUTs, produce a beamformed ultrasonic receiver image, where the one or more blood vessels are identified based, at least in part, on the beamformed ultrasonic receiver image. In some implementations, the array of PMUTs is configured to operate at different resonant frequencies. In some implementations, the encapsulation layer is transparent to the light emitted by the light source system. In some implementations, a thickness of the apparatus is equal to or less than about 4 mm.

Other innovative aspects of the subject matter described in this disclosure can be implemented in a method. The method includes causing a light source system formed on a substrate to emit light towards a target object, receiving, from an ultrasonic receiver system formed on the substrate, signals corresponding to ultrasonic waves caused by a photoacoustic response of the target object to light emitted by the light source system, amplifying the signals corresponding to the ultrasonic waves, producing a beamformed ultrasonic receiver image, and detecting a blood vessel within the target object based, at least in part on the beamformed ultrasonic receiver image. The ultrasonic receiver system comprises an array of piezoelectric micromachined ultrasonic transducers.

In some implementations, the method further includes estimating one or more cardiac features based, at least in part, on the beamformed ultrasonic receiver image. In some implementations, the array of piezoelectric micromachined ultrasonic transducers are configured to operate at different resonant frequencies. In some implementations, the light source system includes one or more vertical cavity surface emitting laser chips. In some implementations, the light source system includes one or more edge-emitting laser chips.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon. The software may include instructions for controlling one or more devices to perform one or more disclosed methods.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale. Like reference numbers and designations in the various drawings indicate like elements.

DETAILED DESCRIPTION

Figure 1:
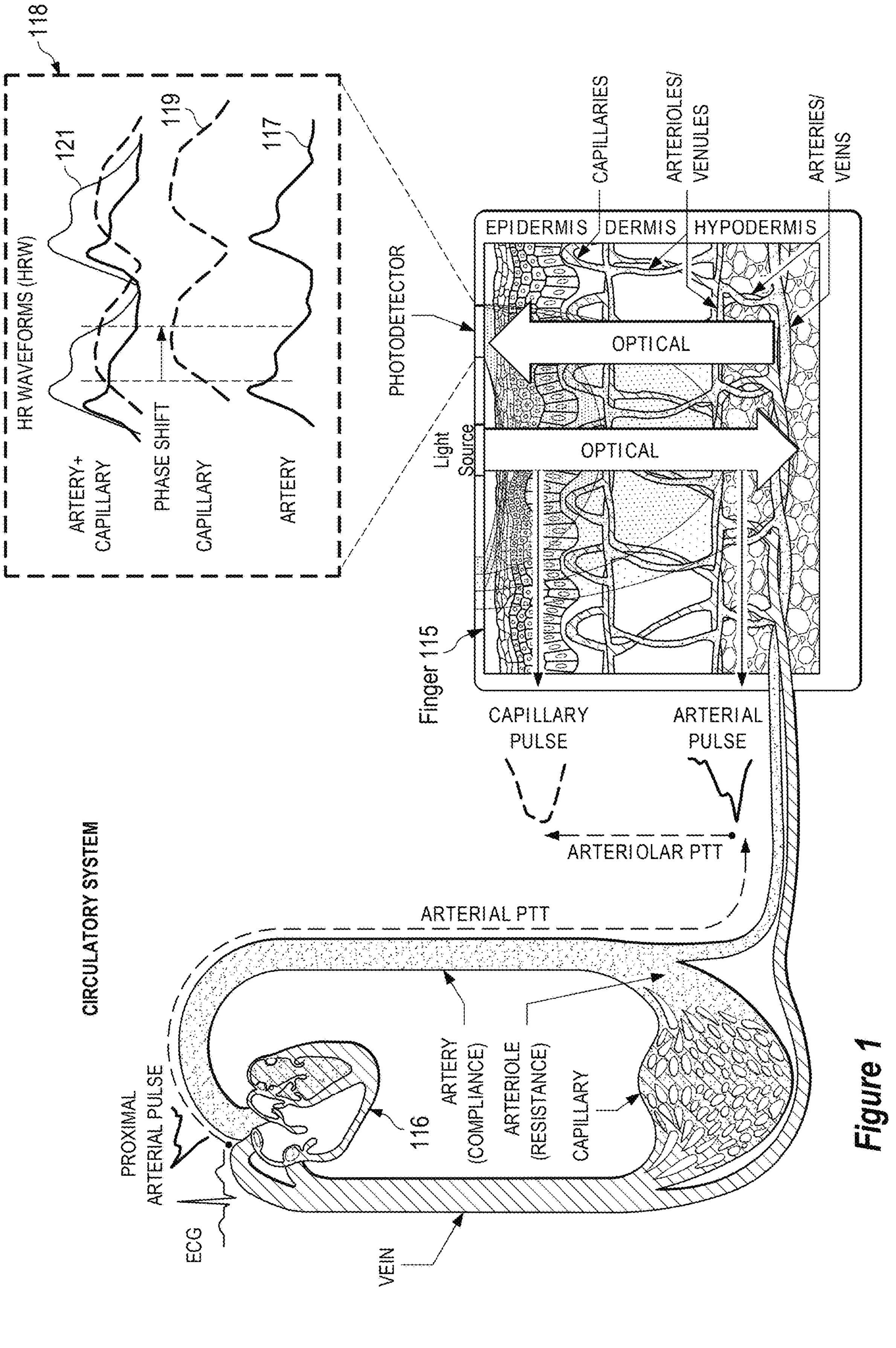
FIG. 1 shows an example of a blood pressure monitoring device based on photoplethysmography (PPG).

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, handheld or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, DVD players, CD players, VCRs, radios, portable memory chips, washers, dryers, washer/dryers, parking meters, automobile doors, autonomous or semi-autonomous vehicles, drones, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

Non-invasive health monitoring devices, such as photoacoustic plethysmography (PAPG)-capable devices, have various potential advantages over more invasive health monitoring devices such as cuff-based or catheter-based blood pressure measurement devices. However, it has proven to be difficult to design satisfactory PAPG-capable devices. One challenge is that several existing PAPG devices are relatively bulky. The size of such devices may render the devices uncomfortable to use. Furthermore, the type of components that are used as light sources in existing PAPG devices may be outdated in at least some cases and it would be desirable to take advantage of current enhancements and technological improvements.

Some "semi-compact" devices may have a length in the range of 5.0 mm to 40 mm. Some semi-compact devices may have a cross-sectional area in the range of 30 $mm^2$ to 50 $mm^2$. A "compact" device is a device that is smaller than a semi-compact device. For example, some semi-compact devices that have recently been developed by the present assignee to mitigate artifact signals such as electromagnetic interference (EMI) signals, signals from reflected light, and signals from reflected acoustic waves, may be too large to deploy conveniently in a wearable device, such as a watch, a patch or an ear bud.

Some disclosed PAPG devices of the present disclosure include an ultrasonic receiver system and a light source system formed on a common substrate. The ultrasonic receiver system includes an array of micromachined ultrasonic transducer elements configured to detect acoustic waves corresponding to a photoacoustic response of a target object to light provided by the light source system. According to some implementations, the array of micromachined ultrasonic transducer elements includes an array of piezoelectric micromachined ultrasonic transducers (PMUTs). In some implementations, an encapsulation layer is disposed over the array of micromachined ultrasonic transducer elements and the light source system, where encapsulation layer is transparent to the light provided by the light source system. Circuitry associated with the light source system and the ultrasonic receiver system may be integrated with the common substrate. In some implementations, the PAPG device further includes a control system formed on the common substrate along with the light source system and the ultrasonic receiver system, where the control system is in electrical communication with the light source system and the ultrasonic receiver system.

Particular implementations of the subject matter described in this disclosure can be implemented to realize one or more of the following potential advantages. Various disclosed configurations include PAPG-capable devices that are compact enough to reside in a wearable device. Having the ultrasonic receiver system and the light source system fabricated on a common substrate reduces form factor to obtain an even more compact design. Accordingly, the PAPG device of the present disclosure achieves integration, miniaturization, and cost reduction, and the PAPG of the present disclosure is easier to integrate into mass production compared to current bulky PAPG devices. Micromachined ultrasonic transducers in an ultrasonic receiver system are able to operate at higher frequencies than traditional receiver stacks, which improves beam-forming and achieves better receiver image quality. Furthermore, an array of micromachined ultrasonic transducers in an ultrasonic receiver system can operate at different resonant frequencies, thereby enabling a larger effective bandwidth. The PAPG device of the present disclosure also enables more array elements of micromachined ultrasonic transducers for improved beam-forming and provides increased flexibility in array geometry.

FIG. 1 shows an example of a blood pressure monitoring device based on photoplethysmography (PPG). FIG. 1 shows examples of arteries, veins, arterioles, venules and capillaries of a circulatory system, including those inside a finger 115. In the example shown in FIG. 1, an electrocardiogram (ECG) sensor has detected a proximal arterial pulse near the heart 116. Some examples are described below of measurement of the arterial pulse transit time (PTT) according to arterial pulses measured by two sensors, one of which may be an electrocardiogram sensor in some implementations.

According to the example shown in FIG. 1, a light source that includes one or more lasers or light-emitting diodes (LEDs) has transmitted light (in some examples, green, red, and/or near-infrared (NIR) light) that has penetrated the tissues of the finger 115 in an illuminated zone. Reflections from these tissues, detected by the photodetector, may be used to detect volumetric changes in the blood of the illuminated zone of the finger 115 that correspond to heart rate waveforms.

As shown in the heart rate waveform graphs 118 of FIG. 1, the capillary heart rate waveform 119 is differently-shaped and phase-shifted relative to the artery heart rate waveform 117. In this simple example, the detected heart rate waveform 121 is a combination of the capillary heart rate waveform 119 and the artery heart rate waveform 117. In some instances, the responses of one or more other blood vessels may also be part of the heart rate waveform 121 detected by a PPG-based blood pressure monitoring device. PPG-based blood pressure monitoring devices are not optimal because PPG superimposes data corresponding to the blood volume of all illuminated blood vessels, each of which exhibit different and time-shifted blood volume changes. Nonetheless, there are many deployed PPG-based blood pressure monitoring devices.

Figure 2:
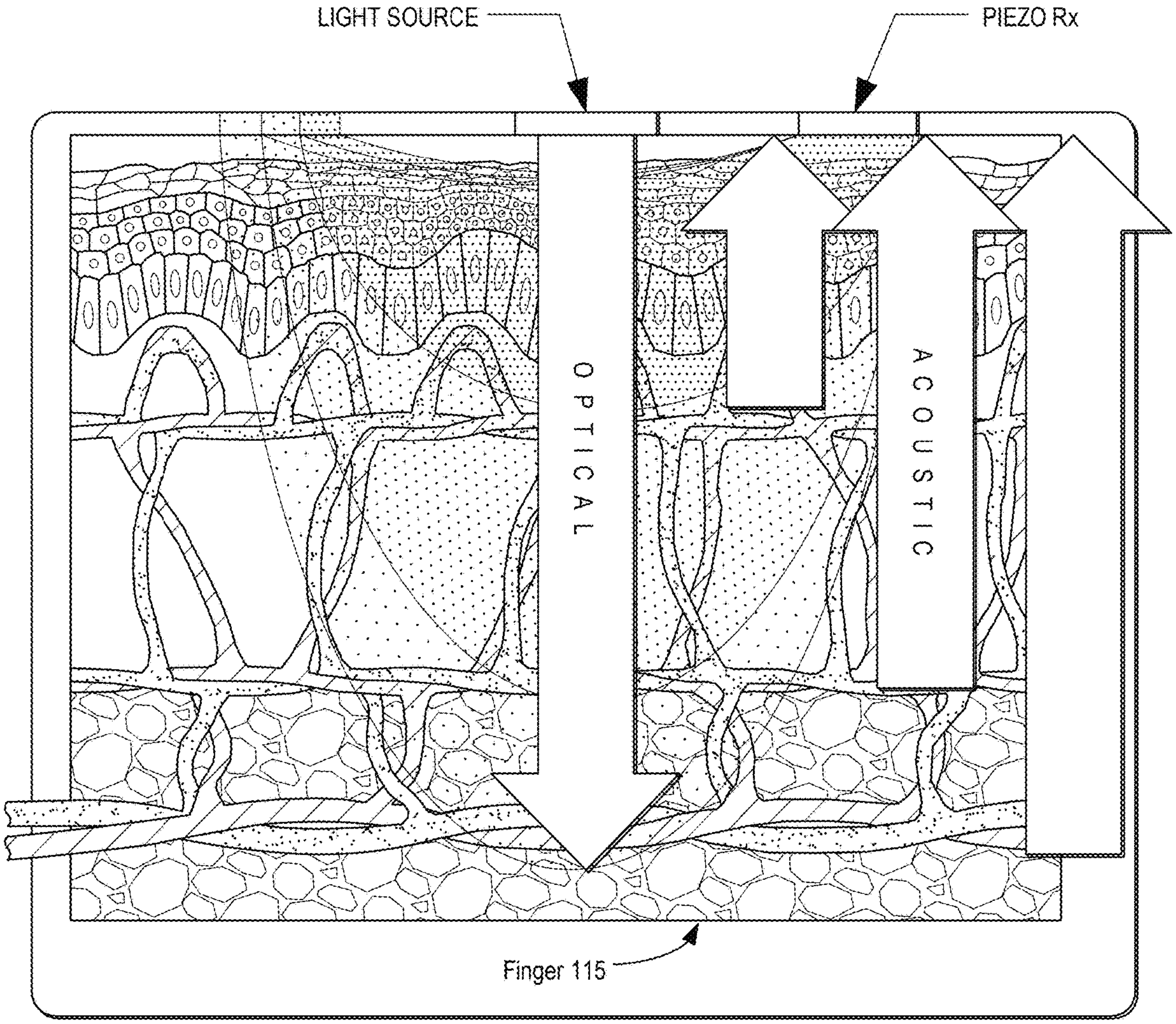
FIG. 2 shows an example of a blood pressure monitoring device based on photoacoustic plethysmography, which may be referred to herein as PAPG.

FIG. 2 shows an example of a blood pressure monitoring device based on photoacoustic plethysmography, which may be referred to herein as PAPG. FIG. 2 shows the same examples of arteries, veins, arterioles, venules and capillaries inside the finger 115 that are shown in FIG. 1. In some examples, the light source shown in FIG. 2 may be, or may include, one or more LEDs, one or more laser diodes, etc. In this example, as in FIG. 1, the light source has transmitted light (in some examples, green, red, and/or near-infrared (NIR) light) that has penetrated the tissues of the finger 115 in an illuminated zone.

In the example shown in FIG. 2, blood vessels (and components of the blood itself) are heated by the incident light from the light source and are emitting acoustic waves. In this example, the emitted acoustic waves include ultrasonic waves. According to this implementation, the acoustic wave emissions are being detected by an ultrasonic receiver, which is a piezoelectric receiver in this example. Photoacoustic emissions from the illuminated tissues, detected by the piezoelectric receiver, may be used to detect volumetric changes in the blood of the illuminated zone of the finger 115 that correspond to heart rate waveforms. Although some of the tissue areas shown to be illuminated are offset from those shown to be producing photoacoustic emissions, this is merely for illustrative convenience. It will be appreciated that that the illuminated tissues will actually be those producing photoacoustic emissions. Moreover, it will be appreciated that the maximum levels of photoacoustic emissions will often be produced along the same axis as the maximum levels of illumination. In some examples, the ultrasonic receiver may be an instance of the ultrasonic receiver system 302 that is described below with reference to FIG. 3.

One important difference between the PPG-based system of FIG. 1 and the PAPG-based method of FIG. 2 is that the acoustic waves shown in FIG. 2 travel much more slowly than the reflected light waves shown in FIG. 1. Accordingly, depth discrimination based on the arrival times of the acoustic waves shown in FIG. 2 is possible, whereas depth discrimination based on the arrival times of the light waves shown in FIG. 1 may not be possible. This depth discrimination allows some disclosed implementations to isolate acoustic waves received from the different blood vessels.

According to some such examples, such depth discrimination allows artery heart rate waveforms to be distinguished from vein heart rate waveforms and other heart rate waveforms. Therefore, blood pressure estimation based on depth-discriminated PAPG methods can be substantially more accurate than blood pressure estimation based on PPG-based methods.

Figure 3:
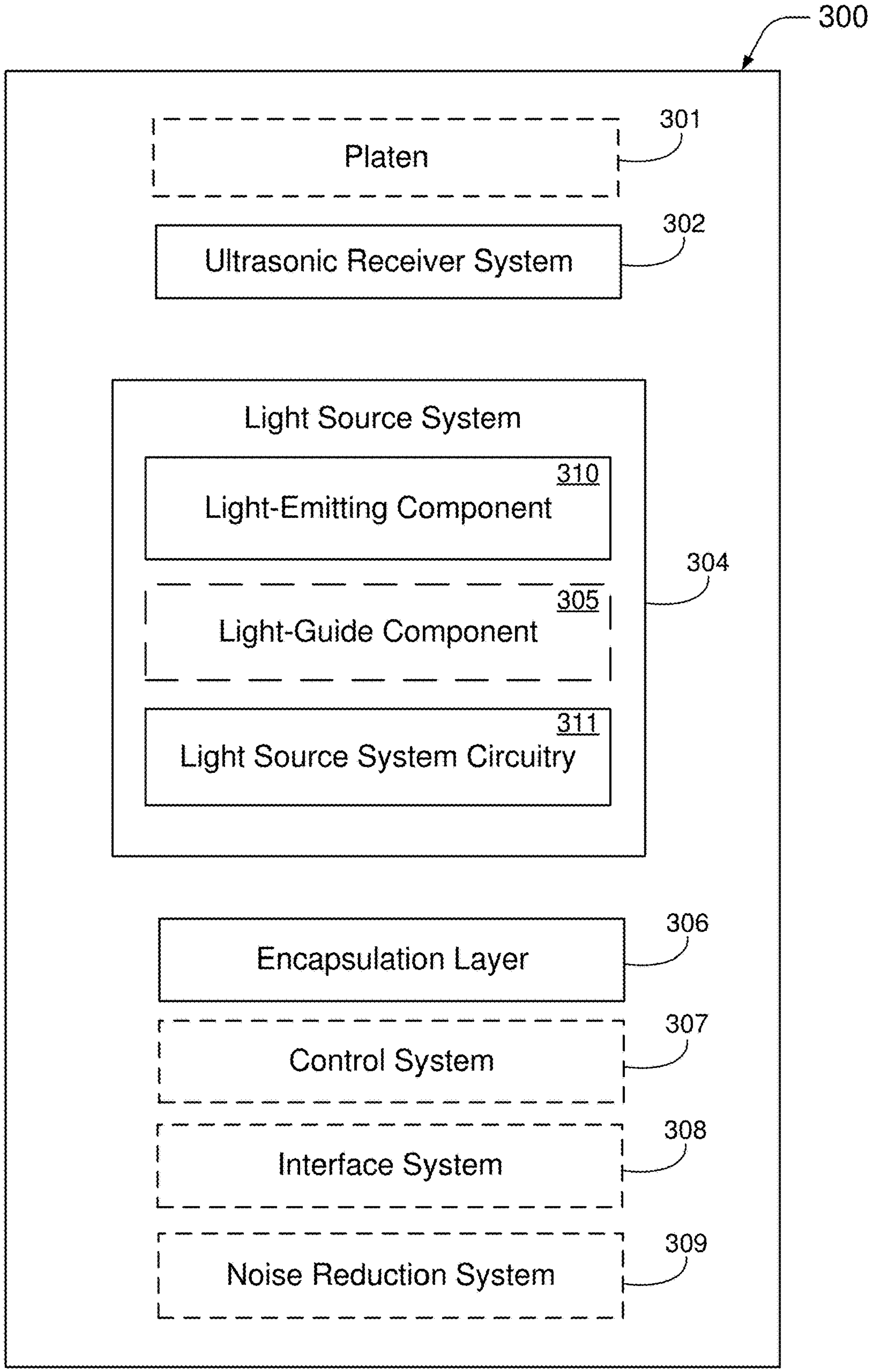
FIG. 3 is a block diagram that shows example components of a photoacoustic apparatus according to some disclosed implementations.

FIG. 3 is a block diagram that shows example components of a photoacoustic apparatus according to some disclosed implementations. In this example, the photoacoustic apparatus 300 includes an ultrasonic receiver system 302, a light source system 304, and an encapsulation layer 306. In some implementations, the light source system 304 can include at least one light-emitting component 310, a light guide component 305, and light source system circuitry 311. In some implementations, the photoacoustic apparatus 300 optionally includes a platen 301. In some implementations, the photoacoustic apparatus 300 optionally includes a control system 307. In some implementations, the photoacoustic apparatus 300 optionally includes an interface system 308. In some implementations, the photoacoustic apparatus 300 optionally includes a noise reduction system 309.

According to various examples, the ultrasonic receiver system 302 includes a microelectromechanical (MEMS) component that includes an array of ultrasonic transducer elements, such as an array of PMUTs, an array of CMUTs, etc. Rather than bulky receiver stacks, micromachined ultrasonic transducers can be fabricated on a semiconductor chip in a thin film MEMS-based process for a miniaturized assembly.

In some implementations, the ultrasonic receiver system 302 may be configured to operate at one or more mean frequencies over a bandwidth range (60% to 90%), such as, for example, one or more mean frequencies selected in a 1-60 MHz range. With an array of ultrasonic transducers, the ultrasonic receiver system 302 may be tuned to operate at higher frequencies than bulky receiver stacks, even up to about 40 MHz, up to about 50 MHz, or even up to about 60 MHz. In some cases, the ultrasonic receiver system 302 is tuned to a mean frequency in a range between about 10 MHz and about 20 MHz.

In some examples, the light source system 304 is configured to emit light towards a target object in contact with or in proximity to the photoacoustic apparatus 300. The light guide component 305 may be arranged to propagate light emitted by the light-emitting component 310.

The light-emitting component 310 may, in some examples, include one or more light-emitting diodes. In some implementations, the light-emitting component 310 may include one or more laser diodes. According to some implementations, the light-emitting component 310 may include one or more multi-junction vertical-cavity surface-emitting lasers (VCSELs). In some implementations, the light-emitting 310 may include one or more edge-emitting lasers (EELs). In some implementations, the light-emitting component 310 may include one or more neodymium-doped yttrium aluminum garnet (Nd:YAG) lasers.

In some examples, the light-emitting component 310 may be configured to emit laser pulses in a wavelength range of 500 nm to 1000 nm. The light-emitting component 310 may, in some examples, be configured to transmit light in one or more wavelength ranges. In some examples, the light-emitting component 310 may configured for transmitting light in a wavelength range of 500 to 600 nanometers (nm). According to some examples, the light-emitting component 310 may be configured for transmitting light in a wavelength range of 800 to 950 nm. In view of factors such as skin reflectance, fluence, the absorption coefficients of blood and various tissues, and skin safety limits, one or both of these wavelength ranges may be suitable for various use cases. For example, the wavelength ranges of 500 nm to 600 nm and of 800 to 950 nm may both be suitable for obtaining photoacoustic responses from relatively smaller, shallower blood vessels, such as blood vessels having diameters of approximately 0.5 mm and depths in the range of 0.5 mm to 1.5 mm, such as may be found in a finger. The wavelength range of 800 to 950 nm may, for example, be suitable for obtaining photoacoustic responses from relatively larger, deeper blood vessels, such as blood vessels having diameters of approximately 2.0 mm and depths in the range of 2 mm to 3 mm, such as may be found in an adult wrist.

The light source system circuitry 311 may include various types of drive circuitry, depending on the particular implementation. In some disclosed implementations, the light-emitting component 310 may include at least one multi-junction laser diode, which may produce less noise than single-junction laser diodes. In some examples, the light source system circuitry 311 may be configured to cause the light-emitting component 310 to emit pulses of light at pulse widths in a range from 3 nanoseconds to 1000 nanoseconds. According to some examples, the light source system circuitry 311 may be configured to cause the light source system to emit pulses of light at pulse repetition frequencies in a range from 1 kilohertz to 100 kilohertz.

In some implementations, the photoacoustic apparatus 300 may include one or more sound-absorbing layers, acoustic isolation material, light-absorbing material, light-reflecting material, or combinations thereof.

In some implementations, the light source system 304 may be configured for emitting various wavelengths of light, which may be selectable to trigger acoustic wave emissions primarily from a particular type of material. For example, because the hemoglobin in blood absorbs near-infrared light very strongly, in some implementations the light source system 304 may be configured for emitting one or more wavelengths of light in the near-infrared range, in order to trigger acoustic wave emissions from hemoglobin. However, in some examples the control system 307 can be a part of that light source system circuitry 311 and can be configured to control the wavelength(s) of light emitted by the light-emitting component 310 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the ultrasonic receiver system 302. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver. Image data from the ultrasonic receiver that is obtained with light sources of different wavelengths and at different depths (e.g., varying RGDs) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose or blood oxygen within a blood vessel inside a target object such as a finger may be detected photoacoustically.

According to some implementations, the light-emitting component 310 may be configured to emit a light pulse with a pulse width less than about 100 nanoseconds. In some implementations, the light pulse may have a pulse width between about 10 nanoseconds and about 500 nanoseconds or more. According to some examples, the light-emitting component 310 may be configured to emit a plurality of light pulses at a pulse repetition frequency between 10 Hz and 100 kHz. Alternatively or additionally, in some implementations the light-emitting component 310 may be configured to emit a plurality of light pulses at a pulse repetition frequency between about 1 MHz and about 100 MHz. Alternatively or additionally, in some implementations the light-emitting component 310 may be configured to emit a plurality of light pulses at a pulse repetition frequency between about 10 Hz and about 1 MHz. In some examples, the pulse repetition frequency of the light pulses may correspond to an acoustic resonant frequency of the ultrasonic receiver and the substrate. For example, a set of four or more light pulses may be emitted from the light-emitting component 310 at a frequency that corresponds with the resonant frequency of a resonant acoustic cavity in the ultrasonic receiver system 302, allowing a build-up of the received ultrasonic waves and a higher resultant signal strength. In some implementations, filtered light or light sources with specific wavelengths for detecting selected materials may be included with the light source system 304. In some implementations, the light source system 304 may contain light sources such as red, green, and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

In some examples, an encapsulation layer 306 serves to protect the ultrasonic receiver system 302 and the light source system 304 from the ambient environment. The encapsulation layer 306 serves as a protection mechanism against shock/vibration and prevents the ultrasonic receiver system 302 and the light source system 304 from directly contacting human skin. The encapsulation layer 306 may be made of any suitable material, such as a polymer material. In some implementations, the encapsulation layer 306 includes polydimethylsiloxane (PDMS) or parylene.

The encapsulation layer 306 may function to provide acoustic coupling with the target object (e.g., human skin). In particular, the encapsulation layer 306 may serve as an acoustic matching layer between the human skin and the ultrasonic receiver system 302. For instance, the encapsulation layer 306 may be configured to approximate an acoustic impedance of human skin. That way, the encapsulation layer 306 provides tissue-matched acoustic coupling. A typical range of acoustic impedances for human skin is 1.53-1.680 MRayls. In some examples, at least an outer surface of the encapsulation layer 306 may have an acoustic impedance that is in the range of 1.4-1.8 MRayls, or in the range of 1.5-1.7 MRayls. In some instances, the encapsulation layer 306 may alternatively or additionally be configured to approximate an acoustic impedance of one or more ultrasonic transducers of the ultrasonic receiver system 302. This increases the performance of the acoustic waves transmitted to the ultrasonic transducers of the ultrasonic receiver system 302.

In some implementations, the encapsulation layer 306 is transparent or substantially transparent to the light emitted by the light source system 304. Substantial transparency as used herein may be defined as transmittance of light of about 70% or more, such as about 80% or more or even about 90% or more. The light source system 304 may be configured to emit light through the encapsulation layer 306 towards the target object in contact with or in proximity with the encapsulation layer 306.

In some examples, an optional platen 301 is provided in addition to the encapsulation layer 306. The platen 301 may be made of any suitable material, such as glass, acrylic, polycarbonate, etc. According to some examples, the platen 301 (or another portion of the apparatus) may include one or more anti-reflective layers. In some examples, one or more anti-reflective layers may reside on, or proximate, one or more outer surfaces of the platen 301. In some examples, at least a portion of the outer surface of the platen 301 may have an acoustic impedance that is configured to approximate an acoustic impedance of human skin. The portion of the outer surface of the platen 301 may, for example, be a portion that is configured to receive a target object, such as a human digit. (As used herein, the terms "finger" and "digit" may be used interchangeably, such that a thumb is one example of a finger.) A typical range of acoustic impedances for human skin is 1.53-1.680 MRayls. In some examples, at least an outer surface of the platen 301 may have an acoustic impedance that is in the range of 1.4-1.8 MRayls, or in the range of 1.5-1.7 MRayls. Alternatively, or additionally, in some examples at least an outer surface of the platen 301 may be configured to conform to a surface of human skin. In some such examples, at least an outer surface of the platen 301 may have material properties like those of putty or chewing gum. In some examples, at least a portion of the platen 301 may have an acoustic impedance that is configured to approximate an acoustic impedance of one or more ultrasonic transducers of the ultrasonic receiver system 302.

In some implementations, the control system 307 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 307 also may include (and/or be configured for communication with) one or more memory devices, such as one or more random access memory (RAM) devices, read-only memory (ROM) devices, etc.

Accordingly, the photoacoustic apparatus 300 may have a memory system that includes one or more memory devices, though the memory system is not shown in FIG. 3. The control system 307 may be configured for receiving and processing data from the ultrasonic receiver system 302. If the photoacoustic apparatus 300 includes an ultrasonic transmitter, the control system 307 may be configured for controlling the ultrasonic transmitter. In some implementations, functionality of the control system 307 may be partitioned between one or more controllers or processors, such as a dedicated sensor controller and an applications processor of a mobile device.

In some examples, the control system 307 may be configured to control the light source system 304. For example, the control system 307 may be configured to control one or more light-emitting portions of the light source system 304 to emit laser pulses. The laser pulses may, in some examples, be in a wavelength range of 500 nm to 1000 nm. The laser pulses may, in some examples, have pulse widths in a range from 3 nanoseconds to 1000 nanoseconds. In some examples, the control system 307 may be configured to receive signals from the ultrasonic receiver system 302 corresponding to the ultrasonic waves generated by the target object responsive to the light from the light source system 304. In some examples, the control system 307 may be configured to estimate one or more cardiac features based, at least in part, on the signals. According to some examples, the cardiac features may be, or may include, blood pressure.

Some implementations of the photoacoustic apparatus 300 may include the interface system 308. In some examples, the interface system 308 may include a wireless interface system. In some implementations, the interface system 308 may include a user interface system, one or more network interfaces, one or more interfaces between the control system 307 and a memory system and/or one or more interfaces between the control system 307 and one or more external device interfaces (e.g., ports or applications processors), or combinations thereof. According to some examples in which the interface system 308 is present and includes a user interface system, the user interface system may include a microphone system, a loudspeaker system, a haptic feedback system, a voice command system, one or more displays, or combinations thereof. According to some examples, the interface system 308 may include a touch sensor system, a gesture sensor system, or a combination thereof. The touch sensor system (if present) may be, or may include, a resistive touch sensor system, a surface capacitive touch sensor system, a projected capacitive touch sensor system, a surface acoustic wave touch sensor system, an infrared touch sensor system, any other suitable type of touch sensor system, or combinations thereof.

According to some examples, the photoacoustic apparatus 300 may include a noise reduction system 309. For example, the noise reduction system 309 may include one or more mirrors that are configured to reflect light from the light source system 304 away from the ultrasonic receiver system 302. In some implementations, the noise reduction system 309 may include one or more sound-absorbing layers, acoustic isolation material, light-absorbing material, light-reflecting material, or combinations thereof. In some examples, the noise reduction system 309 may include acoustic isolation material, which may reside between the light source system 304 and at least a portion of the ultrasonic receiver system 302, on at least a portion of the ultrasonic receiver system 302, or combinations thereof. In some examples, the noise reduction system 309 may include one or more electromagnetically shielded transmission wires. In some such examples, the one or more electromagnetically shielded transmission wires may be configured to reduce electromagnetic interference from circuitry of the light source system 304, receiver system circuitry, or combinations thereof, that is received by the ultrasonic receiver system 302. In some examples, the light source system circuitry 311 may be grounded separately from the receiver system circuitry.

The photoacoustic apparatus 300 may be used in a variety of different contexts, many examples of which are disclosed herein. For example, in some implementations a mobile device may include the photoacoustic apparatus 300. In some such examples, the mobile device may be a smart phone. In some implementations, a wearable device may include the photoacoustic apparatus 300. The wearable device may, for example, be a bracelet, an armband, a wristband, a watch, a ring, a headband or a patch.

Figure 4A:
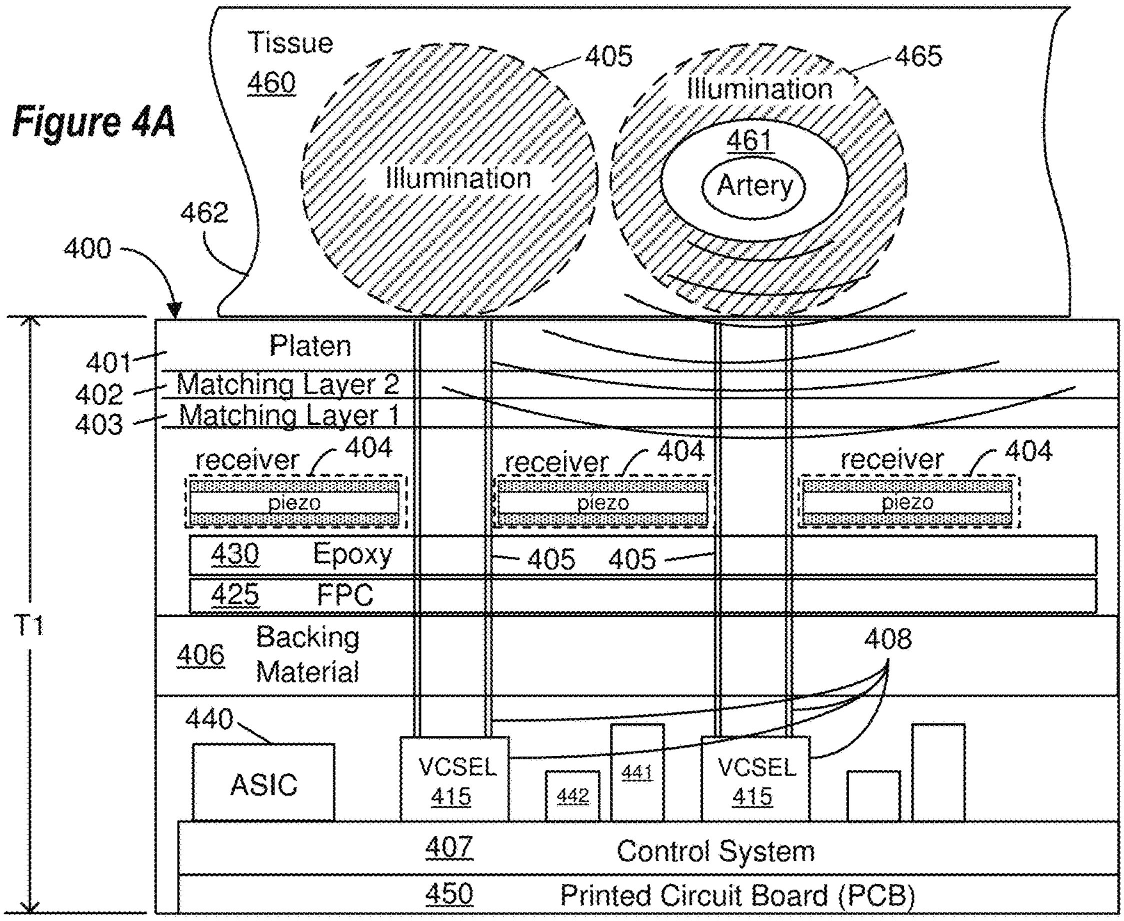
FIG. 4A shows components of a conventional photoacoustic apparatus including an ultrasonic receiver stack, thick backing layer, long light guides, and large light-emitting elements.
Figure 4B:
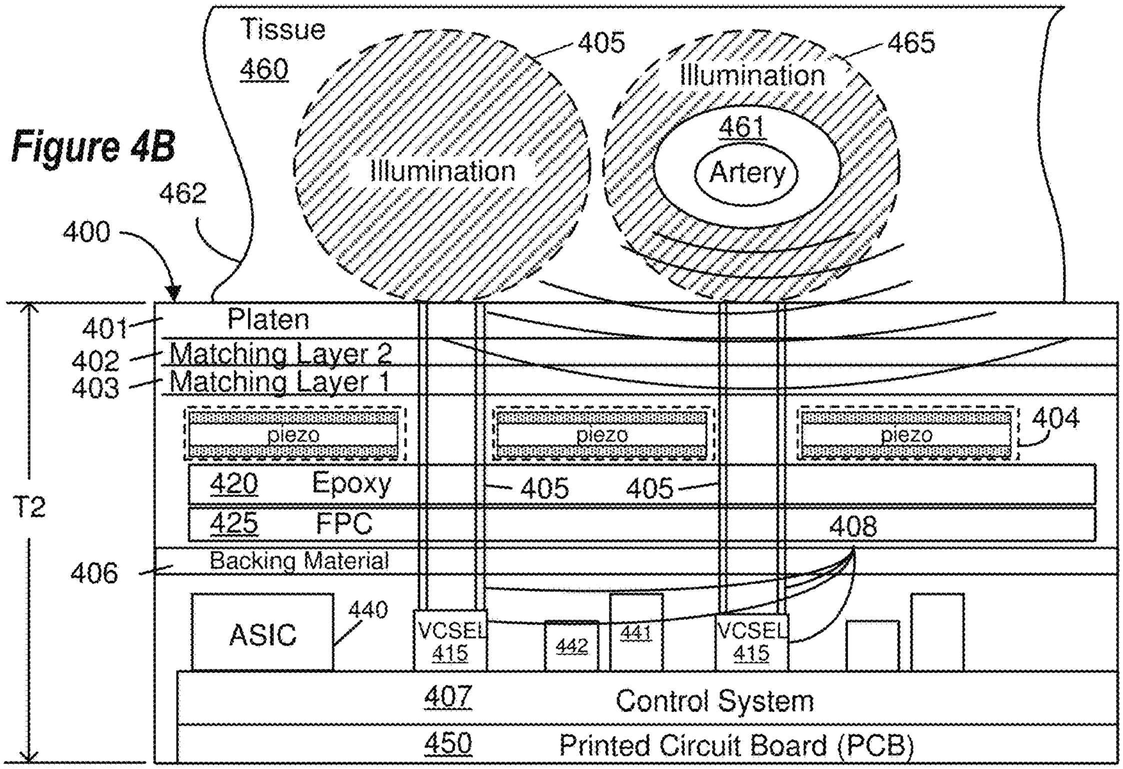
FIG. 4B shows components of a conventional photoacoustic apparatus including an ultrasonic receiver stack, thin backing layer, short light guides, and small light-emitting elements.

FIGS. 4A-4B illustrate previous generations of photoacoustic apparatuses utilizing ultrasonic receiver stacks, matching layers, backing layers, light guides, and light-emitting elements. Traditional ultrasonic receiver stacks include at least a piezoelectric receiver layer, electrode layers, matching layers, and backing layers. This adds to a total thickness of the package of the photoacoustic apparatus. The light source system is integrated with the traditional ultrasonic receiver stacks to form the photoacoustic apparatus. The light source system typically includes light-emitting elements, light guides, spacers, and shielding elements. These elements of the light source system also add to the total thickness of the package of the photoacoustic apparatus. Elements of the light source system and elements of the traditional ultrasonic receiver stacks add to a device's form factor, presenting challenges with their integration in compact devices like smart phones and smart watches.

FIG. 4A shows components of a conventional photoacoustic apparatus including an ultrasonic receiver stack, thick backing layer, long light guides, and large light-emitting elements. In this example, the conventional photoacoustic apparatus 400 includes a platen 401, a receiver stack 404, a light source system 408, and a control system 407. The light source system 408 includes one or more light-emitting components 415 such as VCSELs. The control system 407 can be provided upon circuitry such as a flexible printed circuit (FPC) or printed circuit board (PCB) 450. The control system 407 can include various components such as, for example, an application specific integrated circuit (ASIC) 440, a passive component 441 (e.g., capacitor, resistor, etc.), and an active component 442 (e.g., transistor, integrated circuit, etc.). The ASIC 440 can be designed to perform operations such as, for example, providing control signals to the light-emitting components 415, recording waveforms produced by the receiver stack 404, and transferring data out of the photoacoustic apparatus 400 (to a processor of a computer, for example). In one implementation, the ASIC 440 is a customized component that is optimized for performing operations associated with the photoacoustic apparatus 400. The ASIC 440 can be mounted on the PCB 450 in a configuration that minimizes adverse noise effects.

An outer surface of the platen 401 is configured to receive a target object 462, such as for example, a forearm or a finger, a wrist, etc. In this example, the target object 462 includes tissue 460 and an artery 461. The photoacoustic apparatus 400 can be used to obtain an arterial photoacoustic signal that includes signals from a front portion as well as rear potion of the artery 461, thereby allowing detection of arterial parameters such as, for example, size, diameter, area, etc., with respect to time periods that include distension and straining of the artery 461.

The platen 401 may include any suitable material, such as glass, acrylic, polycarbonate, combinations thereof, etc. According to some examples, a thickness of the platen 401 (in the z direction of the coordinate system shown in FIG. 4A) may be in the range of 50 microns to 500 microns, such as, for example, 150 microns, 200 microns, 250 microns, 300 microns, etc.

The platen 401 can include transparent material and in some examples, may also include one or more anti-reflective layers. In some examples, one or more matching layers may be included between an inner surface of the platen 401 and an interior portion of the photoacoustic apparatus 400. Two example matching layers 402 and 403 may have an acoustic impedance that is selected to reduce the reflections of acoustic waves caused by the acoustic impedance contrast between one or more layers of the receiver stack 404, which are adjacent or proximate the matching layers 402 and 403. According to some examples, the matching layers 402 and 403 may include polyethylene terephthalate (PET).

In this example, the receiver stack 404 includes a piezoelectric layer, a top electrode layer on a first side of the piezoelectric layer, and a bottom electrode on a second side of the piezoelectric layer. In some examples, a layer of anisotropic conductive film (ACF) may reside between each of the electrode layers and the piezoelectric layer. Each of the top electrode layer and the bottom electrode layer can include a conductive material, which may be or may include a conductive metal such as copper. The top and bottom electrode layers may be electrically connected to receiver system circuitry. The receiver system circuitry may be regarded as part of the control system 407. The receiver stack 404 may be mounted upon an FPC 425 by means of an epoxy layer 430. The piezoelectric layer may include a polyvinylidene difluoride (PVDF) polymer a polyvinylidene fluoride-trifluoroethylene (PVDF-TrFE) copolymer, aluminum nitride (AlN), lead zirconate titanate (PZT), piezoelectric composite material such as a 1-3 composite, a 2-2 composite, a 3-3 composite, etc., or combinations thereof.

According to this example, the light source system 408 includes one or more light-emitting components 415. The light-emitting components 415 may, for example, include one or more light-emitting diodes, one or more laser diodes, one or more VCSELs, one or more edge-emitting lasers, one or more neodymium-doped yttrium aluminum garnet (Nd:YAG) lasers, or combinations thereof.

The light-emitting components 415 are configured to transmit light through the light guide components 405 towards the target object 462, which is in contact with the outer surface of the platen 401. An illumination 465 is produced above the outer surface of the platen 401. The illumination 465 illuminates the artery 461 of the target object 462 and produces photoacoustic waves responsive to the illumination 465. The photoacoustic waves travel through the platen 401 and towards the receiver stack 404.

The light guide components 405 may include any suitable material, or combination of materials, for causing at least some of the light emitted by the light-emitting components 415 to propagate within the light guide component 405, for example due to total internal reflection between one or more core materials and one or more cladding materials of the light guide components 405. In such examples, the core material(s) will have a higher index of refraction than the cladding material(s). In one specific and non-limiting example, the core material may have an index of refraction of approximately 1.64 and the cladding material may have an index of refraction of approximately 1.3. In some examples, the core material(s) may include glass, silica, quartz, plastic, zirconium fluoride, chalcogenide, or combinations thereof. According to some examples, the cladding material(s) may include polyvinyl chloride (PVC), acrylic, polytetrafluorocthylene (PTFE), silicone, or fluorocarbon rubber. The light guide components 405 may, in some examples, include one or more optical fibers. The terms "light guide" and "light pipe" may be used herein synonymously.

In some implementations, each of the light guide components 405 may have a substantially uniform cross-section such as a circular cross-section, an oval cross-section, a polygonal cross-section, etc. In some examples, each of the light guide components has a cylindrical shape. With a substantially uniform cross-section, the light guide components 405 may have a non-tapering cross-section. However, in some other implementations, each of the light guide components 405 has a tapering profile. For instance, each of the light guide components 405 may have a larger cross-section at a proximal end of the light guide component 405 that abuts a light-emitting component 415 than at a distal end of the light guide component 405. The larger cross-section may be selected to provide efficient light coupling from the VCSEL into the light guide component 405 and the narrower cross-section may be selected to offer a desirable light dispersion characteristic.

A backing material 406 may be positioned between the control system 407 and the receiver stack 404. In particular, the backing material 406 may reside between the light-emitting components 415 and the FPC 425 of the receiver stack 404. The backing material 406 may be configured to suppress at least some acoustic artifacts and may provide a relatively higher signal-to-noise ratio (SNR) than photoacoustic apparatuses that lack a backing material. The backing material 406 may serve to improve bandwidth and to limit unwanted acoustic reflections from returning back to the receiver stack 404. In some examples, the backing material 406 may include a metal, epoxy, or a combination thereof. In the example photoacoustic apparatus 400, the backing material 406 is shown below the flexible printed circuit 425. In other examples, the backing material 406 may be provided in other places inside the photoacoustic apparatus 400. A thickness of the backing material 406 may be between about 1 mm and about 10 mm, between about 1 mm and about 5 mm, or between about 2 mm and about 5 mm.

A total thickness T1 of the conventional photoacoustic apparatus 400 in FIG. 4A may be between about 5 mm and about 20 mm, between about 7 mm and about 15 mm, or between about 8 mm and about 12 mm. For example, a total thickness T1 of the conventional photoacoustic apparatus 400 in FIG. 4A may be about 10 mm. A part of the thickness T1 is due to the backing material 406, which can add up to 5 mm of thickness. In addition, a part of the thickness T1 is due to the presence of the receiver stack 404 comprising a piezoelectric layer, top electrode layer, and bottom electrode layer. Furthermore, a part of the thickness T1 is due to the matching layers 402 and 403 as well as the platen 401. And, a part of the thickness T1 is due to the length of the light guide components 405 and the size/dimensions of the light-emitting components 415.

Efforts to reduce the total thickness T1 of the photoacoustic apparatus 400 have primarily focused on reducing sizes and dimensions of various components such as the light guide components 405, the backing material 406, receiver stack 404, and light-emitting components 415. Reduction in the total thickness provides a thinner form factor for the photoacoustic apparatus 400.

FIG. 4B shows components of a conventional photoacoustic apparatus including an ultrasonic receiver stack, thin backing layer, short light guides, and small light-emitting elements. A total thickness T2 in FIG. 4B is less than a total thickness T1 in FIG. 4A. The total thickness T2 in FIG. 4B is reduced by shrinking the sizes and dimensions of one or more of the following: the light guide components 405, the receiver stack 404, the light-emitting components 415, and the backing material 406. For example, as shown in FIG. 4B, the backing material 406 is substantially smaller. The thickness of the backing material 406 may be less than about 3 mm, less than about 2 mm, or less than about 1 mm. Also as shown in FIG. 4B, the length of the light guide components 405 may be significantly shorter. The length of the light guide components 405 may be equal to or less than about 5 mm, equal to or less than about 4 mm, or equal to or less than about 3 mm. By shortening the light guide components 405 and using a thinner backing material 406, the total thickness T2 of the photoacoustic apparatus 400 may be shrunk. For example, the total thickness T2 of the photoacoustic apparatus 400 in FIG. 4B may be between about 3 mm and about 10 mm, between about 4 mm and about 8 mm, or between about 4 mm and about 6 mm, thereby reducing a form factor of the photoacoustic apparatus 400. In one example, the total thickness T2 of the photoacoustic apparatus 400 in FIG. 4B is 5 mm.

In some examples, dimensions of the photoacoustic apparatus 400 in FIG. 4B may be reduced by using light-emitting components 415 occupying a smaller area. This further reduces the packaging size of the photoacoustic apparatus 400. By way of an example, the photoacoustic apparatus 400 in FIG. 4A can have dimensions of 16 mm×6 mm×10 mm, and the photoacoustic apparatus 400 in FIG. 4B can have dimensions of 10 mm×6 mm×5 mm.

Earlier generations of photoacoustic apparatuses, such as the photoacoustic apparatus of FIGS. 4A and 4B, have focused primarily on optimizing dimensions of a backing material, a receiver stack, light guide components, and light-emitting components. However, such photoacoustic apparatuses had a total thickness of about 5 mm, about 6 mm, about 7 mm, about 8 mm, about 9 mm, or about 10 mm. The photoacoustic apparatus of the present disclosure achieves a total thickness that is less than about 5 mm, equal to or less than about 4 mm, equal to or less than about 3 mm, or equal to or less than about 2 mm. This further reduces the form factor of the photoacoustic apparatus.

The present disclosure provides a photoacoustic apparatus including an array of micromachined ultrasonic transducers and a light source system on a common substrate. Rather than a bulky ultrasonic receiver stack in the photoacoustic apparatus, the photoacoustic apparatus of the present disclosure includes an ultrasonic receiver system comprising an array of micromachined ultrasonic transducers such as an array of PMUTs, an array of CMUTs, or the like. Instead of light source systems requiring light guide components optically coupled to light-emitting components and configured to direct light towards a target object, the photoacoustic apparatus of the present disclosure includes an in-plane light source system without vertically-oriented light guide components. Such in-plane light source systems may include, for example, VCSEL chips, EEL chips, or the like. The array of micromachined ultrasonic transducers and the in-plane light source system may be formed on the same substrate in a MEMS-based manufacturing process. In some implementations, the photoacoustic apparatus of the present disclosure further includes an encapsulation layer disposed over the array of micromachined ultrasonic transducers and the in-plane light source system.

Figure 5:
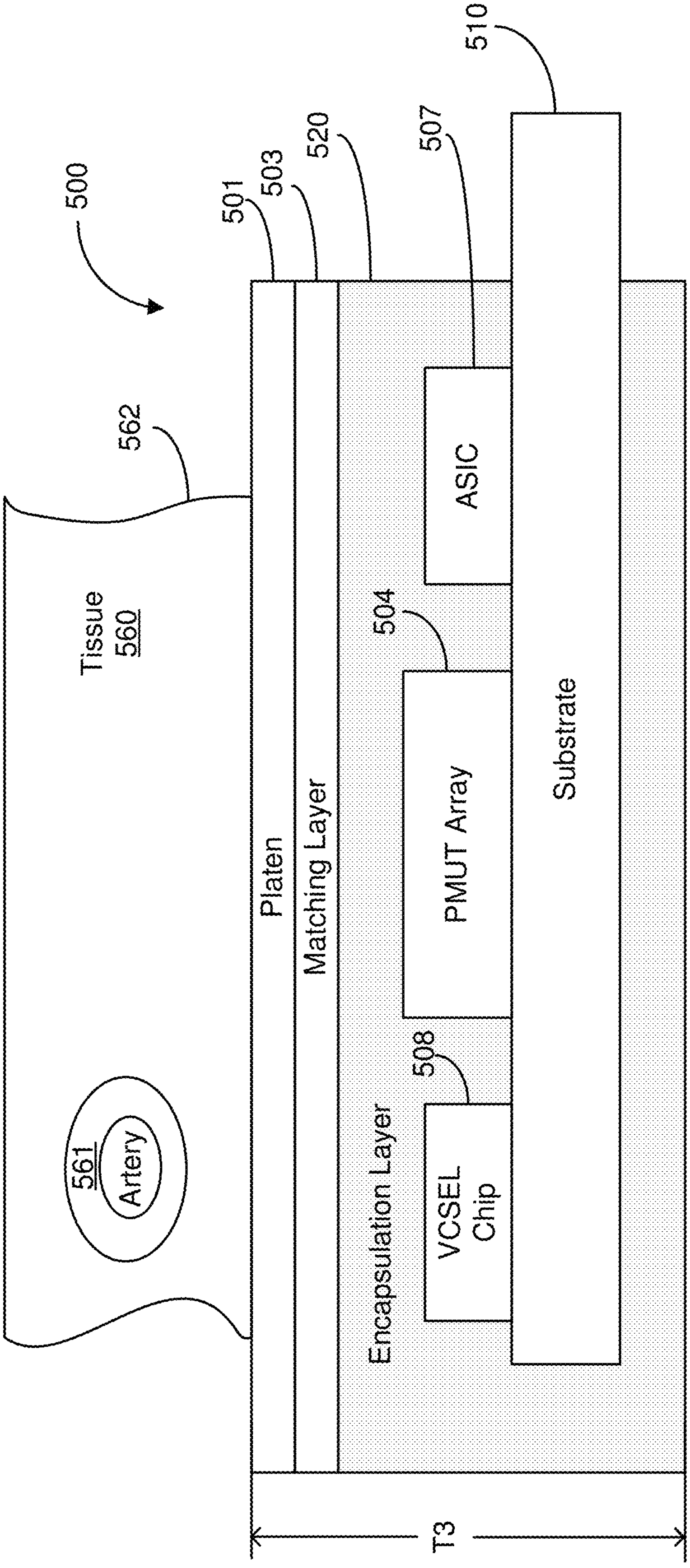
FIG. 5 shows a cross-sectional schematic illustration including example components of a photoacoustic apparatus according to some implementations.

FIG. 5 shows a cross-sectional schematic illustration including example components of a photoacoustic apparatus according to some implementations. The photoacoustic apparatus 500 includes a platen 501, an ultrasonic receiver system 504, an in-plane light source system 508, a control system 507, an encapsulation layer 520, and a substrate 510. The ultrasonic receiver system 504, the in-plane light source system 508, and the control system 507 may be provided on the substrate 510. The encapsulation layer 520 may be disposed over the ultrasonic receiver system 504 and the in-plane light source system 508. In some implementations, the photoacoustic apparatus 500 further includes a matching layer 503 that resides between the platen 501 and the encapsulation layer 520.

An outer surface of the platen 501 is configured to receive a target object 562, such as for example, a forearm or a finger, a wrist, etc. The target object 562 includes tissue 560 and an artery 561. The photoacoustic apparatus 500 can be used to obtain an arterial photoacoustic signal that includes signals from a front portion as well as rear potion of the artery 561, thereby allowing detection of arterial parameters such as, for example, size, diameter, area, etc., with respect to time periods that include distension and straining of the artery 561.

The platen 501 may include any suitable material, such as glass, acrylic, polycarbonate, combinations thereof, etc. According to some examples, a thickness of the platen 501 may be in the range of 50 microns to 500 microns, such as, for example, 150 microns, 200 microns, 250 microns, 300 microns, etc.

The platen 501 can include transparent material and in some examples, may also include one or more anti-reflective layers. In some implementations, one or more matching layers (e.g., matching layer 503) may be included between an inner surface of the platen 501 and the encapsulation layer 520. The matching layer 503 may have an acoustic impedance that is selected to reduce the reflections of acoustic waves caused by the acoustic impedance contrast between the ultrasonic receiver system 504 and the encapsulation layer 520. According to some examples, the matching layer 503 may include PET.

The encapsulation layer 520 may enclose the in-plane light source system 508, the ultrasonic receiver system 504, and the control system 507 within protective material that is transparent to light emitted from the in-plane light source system 508. The encapsulation layer 520 may be located below the platen 501 and/or below the matching layer 503. The encapsulation layer 520 may be disposed over the substrate 510 and, in some cases, may be disposed below the substrate 510 as well. The encapsulation layer 520 may provide protection for sensitive components such as the ultrasonic receiver system 504 against shock/vibration. In some implementations, the encapsulation layer 520 includes PDMS or parylene. In some implementations, the encapsulation layer 520 may have an acoustic impedance that is selected to reduce reflections of acoustic waves and provide acoustic coupling between the target object 562 and the ultrasonic receiver system 504.

The in-plane light source system 508 may include one or more light-emitting chips for emitting light through the encapsulation layer 520 towards the target object 562. Light-emitting chips include semiconductor chips that emit light at a specified wavelength, a plurality of discrete wavelengths, or a broadband range of wavelengths. In some implementations, the light-emitting chips include one or more light-emitting diodes (LEDs). The LED is a semiconductor light source that emits light having a wavelength based on an energy band gap of the semiconductor. In some implementations, the light-emitting chips include one or more lasers. The laser beam may be an ultraviolet laser beam, a visible laser beam, an infrared laser beam, or a mid-infrared laser beam. The visible laser beam at least comprises a red light, a green light, and a blue light. In some implementations, the one or more light-emitting chips include one or more edge emitting laser (EEL) chips. In some implementations, the one or more light-emitting chips include one or more vertical-cavity surface-emitting laser (VCSEL) chips.

In some examples, the in-plane light source system 508 may be configured to emit laser pulses in a wavelength range of 500 nm to 1000 nm. In one example, the one or more light-emitting chips are configured to transmit light in a wavelength range of 500 nm to 600 nm. In another example, the one or more light-emitting chips are configured to transmit light in a wavelength range of 800 nm to 950 nm.

In some implementations, circuitry may be configured to cause the one or more light-emitting chips to emit pulses of light at pulse widths in a range from 3 nanoseconds to 1000 nanoseconds. In some examples, the in-plane light source system 508 may be configured to cause the one or more light-emitting chips to emit pulses of light at pulse repetition frequencies in a range from 1 kHz to 100 KHz.

The control system 507 may control circuitry associated with the in-plane light source system 508. For instance, the control system 507 may be configured to control the wavelength(s) of light emitted by the one or more light-emitting chips, and may preferentially induce acoustic waves in blood vessels, other soft tissue, and/or bones. In some implementations, one or more light-emitting chips of different wavelengths may be fired in turn or simultaneously to generate acoustic emissions that may be detected by the ultrasonic receiver system 504. Image data from the ultrasonic receiver system 504 that is obtained with light-emitting chips of different wavelengths and at different depths (e.g., varying RGDs) into the target object 562 may be combined to determine the location and type of material in the target object 562.

In some implementations, the one or more light-emitting chips may be configured to emit a light pulse with a pulse width less than about 100 nanoseconds. In some implementations, the light pulse may have a pulse width between about 10 nanoseconds and about 500 nanoseconds or more. According to some examples, the light-emitting chips may be configured for emitting a plurality of light pulses at a pulse repetition frequency between 10 Hz and 100 kHz. Alternatively or additionally, in some implementations, the light-emitting chips may be configured to emit a plurality of light pulses at a pulse repetition frequency between about 1 MHz and about 100 MHZ. Alternatively or additionally, in some implementations, the light-emitting chips may be configured to emit a plurality of light pulses at a pulse repetition frequency between about 10 Hz and about 1 MHZ.

The ultrasonic receiver system 504 may include a plurality of ultrasonic transducers such as MEMS transducers. The MEMS transducers may include any one or any combination of PMUTs, CMUTs, and the like. In some implementations, the MEMS transducers include an array of CMUTs. In some implementations, the MEMS transducers include an array of PMUTs. In some implementations, the array of PMUTs may be configured to operate at different resonant frequencies. The MEMS transducers are configured to detect ultrasonic waves generated by the target object 562 in response to irradiation of light from the in-plane light source system 508. For instance, the MEMS transducers may be able to provide a beamformed receiver image of the artery 561 of the target object 562.

The light emitted by the one or more light-emitting chips of the in-plane light source system 508 propagates through the encapsulation layer 520, the matching layer 503, and the platen 501 to the target object 562. Illumination of the artery 561 produces photoacoustic waves responsive to the illumination. The photoacoustic waves travel through the platen 501, the matching layer 503, and the encapsulation layer 520 towards the ultrasonic receiver system 504.

The ultrasonic receiver system 504 may be configured to generate ultrasound data that may be employed to generate a photoacoustic image. The plurality of ultrasonic transducers are formed, positioned, mounted, or otherwise disposed on the substrate 510 such as a semiconductor substrate. The plurality of ultrasonic transducers may be formed on the same substrate or same chip as other electronic components such as the in-plane light source system 508 and the control system 507. Transmit circuitry, receive circuitry, control circuitry, light circuitry, power management circuitry, and processing circuitry may be integrated on the same semiconductor substrate or chip. The control system 507 may receive the ultrasound data and process the ultrasound data from the ultrasonic receiver system 504. For example, the control system 507 may include an ASIC for amplification, beam-forming, and reconstruction of a beamformed receiver image from the ultrasound data. The ASIC may be integrated on the same semiconductor substrate or chip as the in-plane light source system 508 and the ultrasonic receiver system 504.

In some implementations, the control system 507 may include one or more processors and one or more memory devices, such as one or more RAM devices, one or more ROM devices, etc. The control system 507 may be configured for receiving and processing data from the ultrasonic receiver system 504. Additionally or alternatively, the control system 507 may be configured for controlling the light emitted by the in-plane light source system 508. In some implementations, functionality of the control system 507 may be partitioned between one or more controllers or processors, such as a dedicated sensor controller and an applications processor of a mobile device.

In some examples, the control system 507 may be configured to receive signals from the ultrasonic receiver system 504 corresponding to ultrasonic waves generated by the target object 562 in response to the light from the in-plane light source system 508. In some implementations, the control system 507 is further configured to amplify the ultrasonic receiver signals, produce a beamformed ultrasonic receiver image from the ultrasonic receiver signals, and detect a blood vessel (e.g., artery 561) within the target object 562 based at least in part on the beamformed ultrasonic receiver image. In some implementations, the control system 507 is configured to cause the in-plane light source system 508 to emit light towards the target object 562, receive ultrasonic receiver signals from the ultrasonic receiver system 504 corresponding to ultrasonic waves generated by the target object 562, and identify one or more blood vessels (e.g., artery 561) from the ultrasonic receiver signals. In some examples, the control system 507 may be configured to estimate one or more cardiac features based, at least in part, on the ultrasonic receiver signals. For instance, the cardiac features may be, or may include, blood pressure.

The control system 507 may be formed on or part of the substrate 510. The substrate 510 may include a printed circuit board. The substrate 510 may include a ceramic material or a semiconductor material such as silicon. The printed circuit board may include conductive traces and/or wiring for communicating with circuitry corresponding to the in-plane light source system 508 and the ultrasonic receiver system 504. Alternatively, the substrate 510 may include a combination of a printed circuit board and a flexible circuit board, or a combination of a printed circuit board and a non-rigid circuit board. In some implementations, the substrate 510 may include plural conductive traces, active or passive components, integrated circuits, etc. Circuitry in the substrate 510 may be in electrical communication with the in-plane light source system 508 for driving the one or more light-emitting chips, and the circuitry in the substrate 510 may be in electrical communication with the ultrasonic receiver system 504 for receiving, amplifying, and processing signals from the ultrasonic transducers of the ultrasonic receiver system 504.

The one or more light-emitting chips of the in-plane light source system 508 and the array of ultrasonic transducers of the ultrasonic receiver system 504 may be formed on a common substrate such as the substrate 510. In addition, the control system 507 that may include an ASIC chip may also be arranged on the common substrate. Fabrication of such elements on the common substrate simplifies assembly and reduces the cost of manufacturing. CMUTs, PMUTs, light-emitting chips such as VCSEL chips, ASIC chips can be fabricated on the same semiconductor substrate, allowing for greater production in scale and batch processing. In other words, integration of the aforementioned chips (e.g., CMUTs, PMUTs, light-emitting chips, ASIC chips, etc.) may occur on the same wafer. The wafer may be diced to form several sensor dies each assembled with at least the in-plane light source system 508 that includes one or more light-emitting chips, the ultrasonic receiver system 504 that includes a plurality of ultrasonic transducers, and the control system 507 that includes the ASIC chip.

The arrangement of the photoacoustic apparatus 500 may provide a compact design that reduces the footprint and reduces the form factor. Miniaturization of the photoacoustic apparatus 500 is achieved by arranging the receiver components and the optical components to be assembled on the same semiconductor substrate. A total thickness T3 of the photoacoustic apparatus 500 is less than about 5 mm, equal to or less than about 4 mm, equal to or less than about 3 mm, or equal to or less than about 2 mm. In one example, the total thickness T3 is about 4 mm. In another example, the total thickness T3 is about 2 mm. In some implementations, the photoacoustic apparatus 500 in FIG. 5 can have dimensions of 8 mm×4 mm×4 mm.

The ultrasonic transducers in the ultrasonic receiver system of the present disclosure may be an array of PMUTs. PMUTs in the photoacoustic apparatus replace bulky receiver stacks, allowing for tens and hundreds and even thousands of tiny receivers that act as membranes for receiving acoustic signals. The array of PMUTs in the photoacoustic apparatus may provide smaller pixels compared to bulky receiver stacks, that enable higher frequencies and that ultimately enable higher resolution for improved imaging. Each of the PMUT chips has a thickness on the order of microns, such as equal to or less than about 500 μm, or between about 100 μm to about 300 μm. Within a chip, the array of PMUTs may have a lateral dimension equal to or less than about 20 mm, equal to or less than about 15 mm, or equal to or less than about 10 mm. An example of a PMUT chip is described below with respect to FIG. 6.

Figure 6:
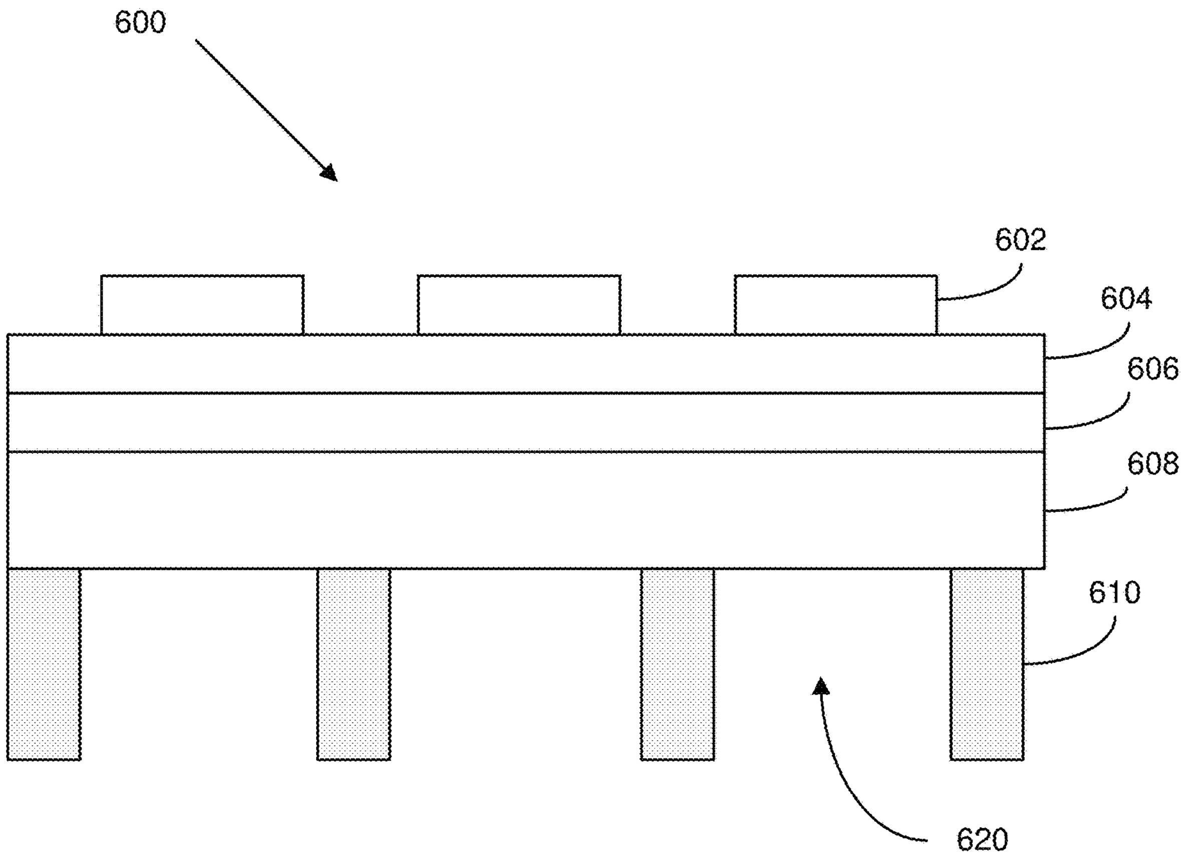
FIG. 6 shows a cross-sectional schematic illustration of an example piezoelectric micromachined ultrasonic transducer (PMUT) chip according to some implementations.

FIG. 6 shows a cross-sectional schematic illustration of an example piezoelectric micromachined ultrasonic transducer (PMUT) chip according to some implementations. PMUTs are MEMS-based piezoelectric ultrasonic transducers that can be fabricated into large arrays with a relatively small footprint.

A PMUT chip 600 includes a thin-film piezoelectric membrane sandwiched between two electrodes, a passive elastic layer, and a substrate, where a resonant cavity may be formed in the substrate. As shown in FIG. 6, the PMUT chip 600 includes a piezoelectric membrane layer 604, where the piezoelectric membrane layer 604 is supported by a substrate 610. A top electrode layer 602 is disposed on a top side (first side) of the piezoelectric membrane layer 604. A bottom electrode layer 606 is disposed on a bottom side (second side) of the piezoelectric membrane layer 604. Usually, metals such as gold (Au), platinum (Pt), titanium (Ti), molybdenum (Mo), chromium (Cr), or combinations thereof, are used as electrode materials. When an electric field is applied between the top electrode layer 602 and the bottom electrode layer 606, the piezoelectric membrane layer 604 can expand and contract due to the piezoelectric effect. The piezoelectric membrane layer 604 may undergo one or both of flexural motion and vibration when the PMUT chip receives ultrasonic signals. Examples of materials in the piezoelectric membrane layer 604 include but are not limited to aluminum nitride (AlN), aluminum scandium nitride (AlScN), lead zirconate titanate (PZT), lithium niobate ($LiNiO_3$), zinc oxide (ZnO), and a co-polymer such as polyvinylidene fluoride (PVDF).

The piezoelectric membrane layer 604 may be disposed over a passive layer 608. The passive layer 608 may be an elastic mechanical layer that is disposed over a resonant cavity 620. The passive layer 608, together with the piezoelectric membrane layer 604, forms a membrane over the resonant cavity 620. The passive layer 608 may be formed of an electrically insulating material such as an oxide (e.g., silicon oxide) or polymer.

The substrate 610 may include a semiconductor substrate such as silicon. One or more resonant cavities 620 may be formed in the substrate 610. In some cases, the resonant cavities 620 may be enclosed by the substrate 610. A resonant frequency of a PMUT is closely related to an aperture size and thickness of a diaphragm defined by each of the resonant cavities 620. Resonant frequency and sensitivity are two important indicators of a performance of a PMUT chip 600. In general, resonant frequency is increased with reduction of diaphragm size, increase of membrane thickness or thickness associated with the resonant cavity 620. In some implementations, the PMUT chip 600 includes circular diaphragms associated with each resonant cavity 620. In some implementations, the PMUT chip 600 includes square diaphragms associated with each resonant cavity 620. Accordingly, resonant frequency or frequencies can be easily tuned by changing dimensions of the one or more resonant cavities 620 in the PMUT chip 600.

In some implementations, the PMUT chip 600 can be configured to operate at a single resonant frequency or mean frequency. The PMUT chip 600 may be configured to operate at high frequencies. For example, the PMUT chip 600 may be configured to operate at frequencies up to about 40 MHz, up to about 50 MHz, or even up to about 60 MHz. In some cases, the PMUT chip 600 is tuned to a mean frequency in a range between about 10 MHz and about 20 MHz. In some implementations, the PMUT chip 600 can be configured to operate at different resonant frequencies. This allows for different resonant frequencies to merge their transmission bands into a larger effective bandwidth.

In some implementations, variations in the PMUT chip 600 can include usage of a self-curved PMUT or pre-curved PMUT. Curve-shaped diaphragms can improve electromechanical coupling and boost acoustic pressure to increase performance. In some implementations, variations in the PMUT chip 600 can include usage of a “bimorph” PMUT, where the “bimorph” structure includes two active layers of piezoelectric materials that can be sandwiched between three thin electrodes. The “bimorph” design can increase drive sensitivity and improve electromechanical coupling.

The PMUT chip 600 can advantageously provide for tens, hundreds, or even thousands of PMUTs that act as tiny pixels. With so many tiny pixels, this improves beamforming and time-domain resolutions, which increases the quality of imaging by combining time-domain and location information. Furthermore, the PMUT chip 600 can advantageously add versatility in terms of fabrication. Many PMUTs can be fabricated at scale and batch processed, simplifying production and reducing the cost of manufacturing.

Figure 7:
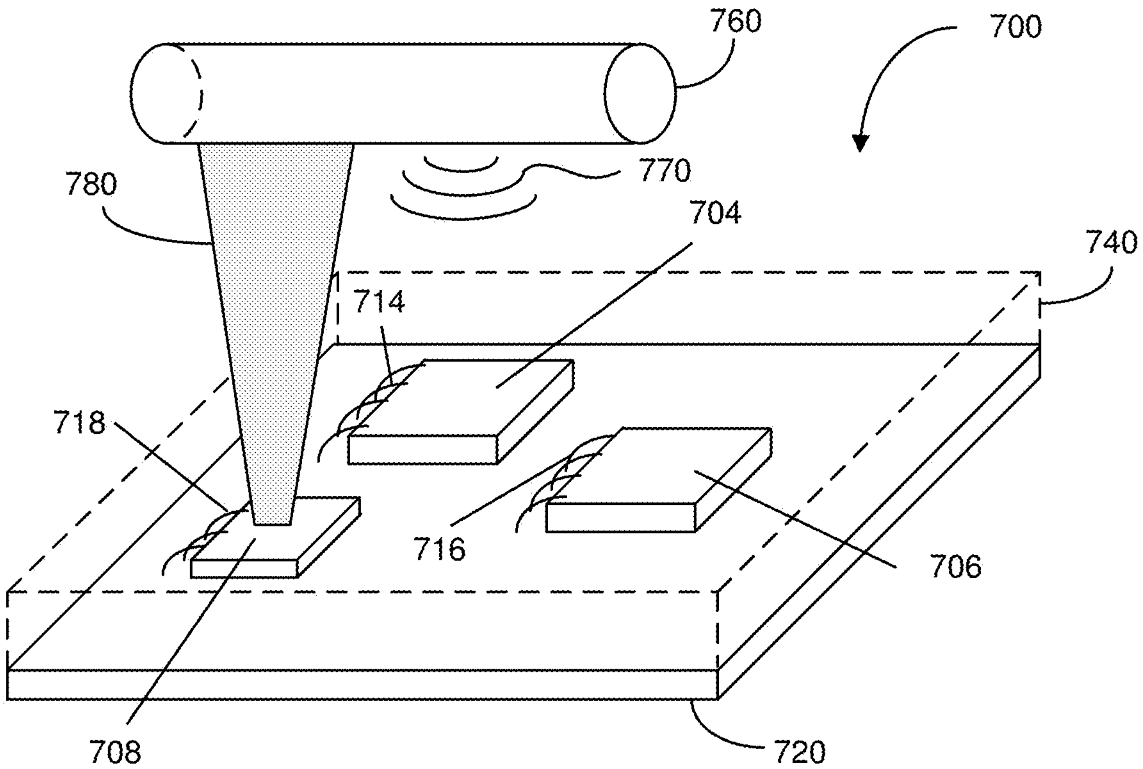
FIG. 7 shows an isometric view of a schematic illustration of an example photoacoustic apparatus including a vertical-cavity surface-emitting laser (VCSEL) chip and a PMUT chip on a substrate according to some implementations.

FIG. 7 shows an isometric view of a schematic illustration of an example photoacoustic apparatus including a vertical cavity surface emitting laser (VCSEL) chip and a PMUT chip on a substrate according to some implementations. The photoacoustic apparatus 700 includes a substrate 720 on which a VCSEL chip 708, ASIC chip 706, and PMUT chip 704 are formed. The substrate 720 may comprise a structure for mechanical support as well as electrical connectivity between components. In some implementations, the substrate 720 comprises a semiconductor material such as silicon. In some implementations, the substrate 720 comprises a printed circuit board or a flexible circuit board. In some implementations, the substrate 720 comprises a ceramic material and/or high temperature dielectric material. The substrate 720 may incorporate electronics and circuitry for providing electrical connectivity between the VCSEL chip 708 and the ASIC chip 706, between the PMUT chip 704 and the ASIC chip 706, and/or between the VCSEL chip 708 and the PMUT chip 704.

The photoacoustic apparatus 700 further includes an encapsulation layer 740 over the VCSEL chip 708, the ASIC chip 706, and the PMUT chip 704. The encapsulation layer 740 provides protection against the ambient environment and prevents the VCSEL chip 708, the ASIC chip 706, and the PMUT chip 704 from directly contacting human skin. The encapsulation layer 740 protects the VCSEL chip 708, the ASIC chip 706, and the PMUT chip 704 against external shock/vibration. In addition, the encapsulation layer 740 electrically insulates circuitry on the substrate 720, including light system wiring 718, control system wiring 716, receiver system wiring 714, and any electrical components. In some implementations, the encapsulation layer 740 provides acoustic coupling with human skin, where an acoustic impedance of the encapsulation layer 740 may approximate human skin. In some examples, the encapsulation layer 740 includes an electrical insulating polymer material such as PDMS or parylene.

The VCSEL chip 708 is configured to emit light 780 through the encapsulation layer 740 towards a blood vessel 760 in human tissue. The encapsulation layer 740 is transparent or at least substantially transparent to the light emitted by the VCSEL chip 708. The VCSEL chip 708 may include multiple laser diodes arranged in an array. In some implementations, the array of laser diodes may be configured to emit light 780 at different wavelengths. In some implementations, the VCSEL chip 708 may be configured to emit light 780 at a specified wavelength. In some examples, the VCSEL chip 708 is configured to emit laser pulses in a wavelength range of 500 nm to 1000 nm. In some implementations, the VCSEL chip 708 is configured to emit pulses of light at pulse widths in the range from 3 nanoseconds to 1000 nanoseconds. Pulse repetition frequencies may range from 10 Hz to 100 kHz, from 1 MHz to 100 MHz, from 1 kHz to 100 kHz, or from 10 Hz to 1 MHZ.

The ASIC chip 706 may control the VCSEL chip 708 to emit light 780 at a desired wavelength, pulse width, pulse rate, power level, or combinations thereof. The ASIC chip 706 may control the VCSEL chip 708 to emit light 780 towards a selected area so that ultrasonic receiver signals may be obtained from the selected area. The blood vessel 760 is illuminated and produces photoacoustic waves 770 responsive to the illumination. The photoacoustic waves 770 travel through the encapsulation layer 740 towards the PMUT chip 704.

The PMUT chip 704 is configured to detect the photoacoustic waves 770 corresponding to the photoacoustic response of the blood vessel 760 to the light 780 provided by the VCSEL chip 708. The PMUT chip 704 may include an array of PMUTs. In some implementations, the array of PMUTs in the PMUT chip 704 may be configured to operate at a single resonant frequency. In some implementations, the array of PMUTs in the PMUT chip 704 may be configured to operate at different resonant frequencies. In some examples, the array of PMUTs may be configured to operate at resonant frequencies between 1 MHz and 80 MHz, between 1 MHz and 60 MHz, between 1 MHz and 40 MHZ, or between 10 MHz and 20 MHz. Operating at multiple different resonant frequencies can increase the bandwidth of the photoacoustic apparatus 700.

The PMUT chip 704 may include a piezoelectric layer sandwiched between a top electrode and a bottom electrode disposed over a passive layer and a supporting silicon substrate. In some implementations, the piezoelectric layer is selected from a group consisting of: aluminum nitride, aluminum scandium nitride, lead zirconate titanate, lithium niobate, zinc oxide, and co-polymer such as PVDF. In some implementations, the PMUT chip 704 may include a bimorph PMUT design. In some implementations, the PMUT chip 704 may include a pre-curved or self-curved PMUT design. In some implementations, a cavity side of the PMUT chip 704 may be oriented to be facing the blood vessel 760. In some implementations, the PMUT chip 704 may be transparent to the light 780 emitted by the VCSEL chip 708. In such cases, the PMUT chip 704 may even be arranged over the VCSEL chip 708 on the substrate 720.

In some implementations, the PMUT chip 704 may be replaced with another micromachined ultrasonic transducer element such as a CMUT chip. By principle, CMUTs utilize a parallel plate capacitor that includes at least two electrodes and employ a high bias voltage.

The photoacoustic waves 770 detected by the PMUT chip 704 are converted into electrical charges in the form of ultrasonic receiver signals or ultrasonic data. The ASIC chip 706 is configured to receive ultrasonic receiver signals from the PMUT chip 704. In some implementations, the ASIC chip 706 processes the ultrasonic receiver signals, amplifies the ultrasonic receiver signals, produces a beamformed ultrasonic receiver image from the ultrasonic receiver signals, and detects the blood vessel 760 based at least in part on the beamformed ultrasonic receiver image. In some implementations, the ASIC chip 706 processes the ultrasonic receiver signals to allow for detection of arterial parameters such as, for example, size, diameter, area, etc. with respect to time periods that include distension and straining of the blood vessel 760. The ultrasonic receiver signals can be used to obtain information of blood flow/distension along a length of the blood vessel 760, thereby allowing for calculating of a pulse wave velocity. In some implementations, the ASIC chip 706 processes the ultrasonic receiver signals, produces a beamformed ultrasonic receiver image from the ultrasonic receiver signals, and estimates one or more blood vessel features based at least in part on the beamformed ultrasonic receiver image. The one or more blood vessel features may include blood vessel diameter, blood vessel area, blood vessel profile, blood vessel distension, volumetric flow, pulse wave velocity, blood vessel wall thickness, or combinations thereof.

Figure 8:
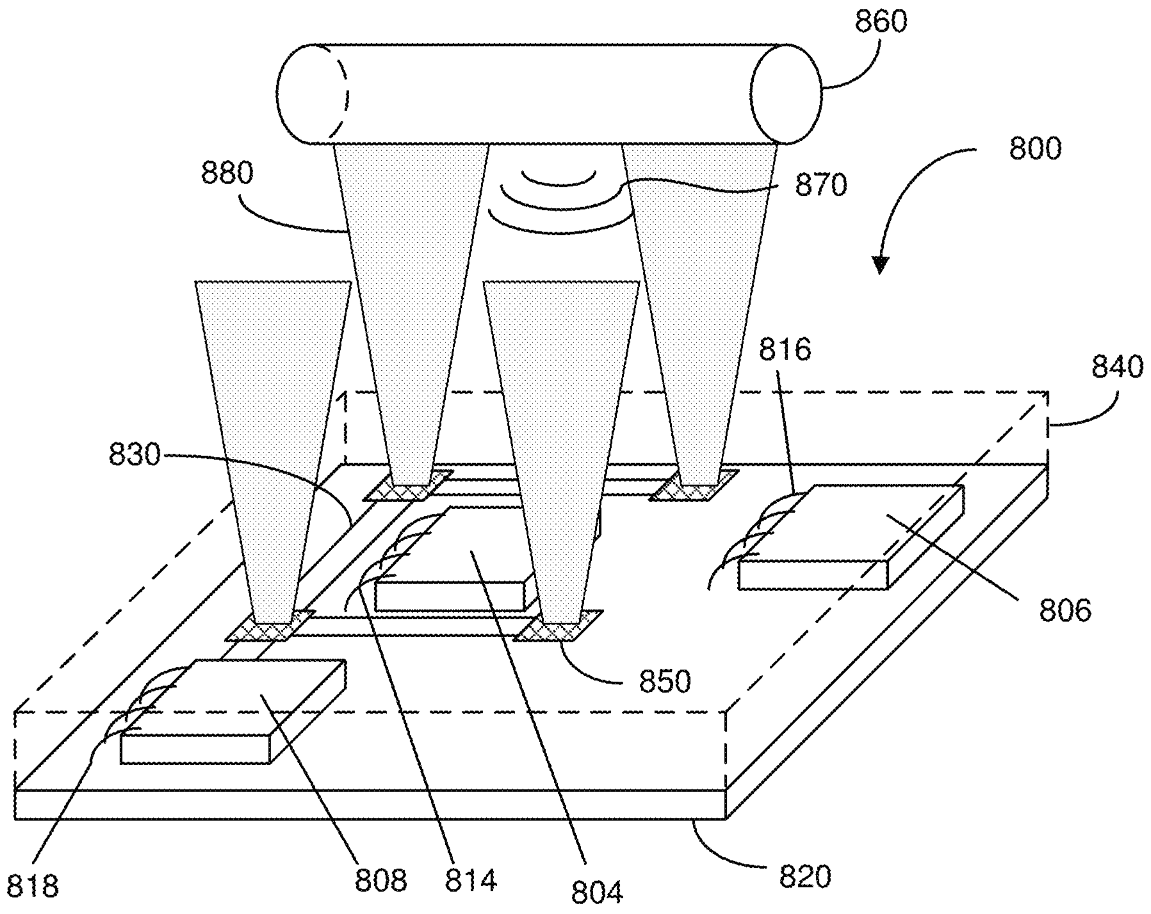
FIG. 8 shows an isometric view of a schematic illustration of an example photoacoustic apparatus including an edge emitting laser (EEL) chip and a PMUT chip on a substrate according to some implementations.

In some implementations, the VCSEL chip 708 may be replaced with another light-emitting chip such as an EEL chip. FIG. 8 shows an isometric view of a schematic illustration of an example photoacoustic apparatus including an edge emitting laser (EEL) chip and a PMUT chip on a substrate according to some implementations. The photoacoustic apparatus 800 includes a substrate 820 on which an EEL chip 808, ASIC chip 806, and PMUT chip 804 are formed. The substrate 820 may comprise a structure for mechanical support as well as electrical connectivity between components. In some implementations, the substrate 820 includes a printed circuit board or a flexible circuit board. In some implementations, the substrate 820 includes a ceramic material and/or high temperature dielectric material. The substrate 820 may incorporate electronics and circuitry for providing electrical connectivity between the EEL chip 808 and the ASIC chip 806, between the PMUT chip 804 and the ASIC chip 806, and/or between the EEL chip 808 and the PMUT chip 804.

The photoacoustic apparatus 800 further includes an encapsulation layer 840 over the EEL chip 808, the ASIC chip 806, and the PMUT chip 804. The encapsulation layer 840 provides protection against the ambient environment and prevents the EEL chip 808, the ASIC chip 806, and the PMUT chip 804 from directly contacting human skin. The encapsulation layer 840 protects the EEL chip 808, the ASIC chip 806, and the PMUT chip 804 against external shock/vibration. In addition, the encapsulation layer 840 electrically insulates circuitry on the substrate 820, including light system wiring 818, control system wiring 816, receiver system wiring 814, and any electrical components. In some implementations, the encapsulation layer 840 provides acoustic coupling with human skin, where an acoustic impedance of the encapsulation layer 840 may approximate human skin. In some examples, the encapsulation layer 840 includes an electrical insulating polymer material such as PDMS or parylene.

The EEL chip 808 is configured to emit light 880 through the encapsulation layer 840 towards a blood vessel 860 in human tissue. The encapsulation layer 840 is transparent or at least substantially transparent to the light emitted by the EEL chip 808. The EEL chip 808 is configured to emit light into one or more light guides 830. In this example, the one or more light guides 830 can include multiple optical fibers or multiple waveguides. The light guides 830 route the light from the EEL chip 808 to one or more diffraction gratings 850 distributed on the substrate 820. In some implementations, the one or more diffraction gratings 850 include reflective or semi-reflective mirrors. The one or more diffraction gratings 850 extract and direct light 880 towards the blood vessel 860 in the human tissue.

As shown in FIG. 8, a plurality of light guides 830 and a plurality of diffraction gratings 850 are provided to couple light to the human tissue at different locations. The plurality of light guides 830 route light from one or more EEL chips 808 to multiple areas located on a plane of the substrate 820. The plurality of diffraction gratings 850 optically coupled to the plurality of light guides 830 are configured to direct light from each of the multiple areas to the target object (e.g., blood vessel 860). This can provide more uniform light illumination around the PMUT chip 804. In other words, the EEL chip 808 with light guides 830 and diffraction gratings 850 can provide a more uniform light distribution compared to spot sources like VCSELs for illumination of the blood vessel 860.

In some implementations, the EEL chip 808 may be configured to emit light 880 at different wavelengths. In some implementations, the EEL chip 808 may be configured to emit light 880 at a specified wavelength. In some examples, the EEL chip 808 is configured to emit laser pulses in a wavelength range of 500 nm to 1000 nm. In some implementations, the EEL chip 808 is configured to emit pulses of light at pulse widths in the range from 3 nanoseconds to 1000 nanoseconds. Pulse repetition frequencies may range from 10 Hz to 100 kHz, from 1 MHz to 100 MHz, from 1 kHz to 100 kHz, or from 10 Hz to 1 MHZ.

The ASIC chip 806 may control the EEL chip 808 to emit light 880 at a desired wavelength, pulse width, pulse rate, power level, or combinations thereof. The ASIC chip 806 may control the EEL chip 808 to emit light 880 towards a selected area(s) so that ultrasonic receiver signals may be obtained from the selected area(s). The blood vessel 860 is more uniformly illuminated and produces photoacoustic waves 870 responsive to the illumination. The photoacoustic waves 870 travel through the encapsulation layer 840 towards the PMUT chip 804.

The PMUT chip 804 is configured to detect the photoacoustic waves 870 corresponding to the photoacoustic response of the blood vessel 860 to the light 880 provided by the EEL chip 808. The PMUT chip 804 may include an array of PMUTs. In some implementations, the array of PMUTs in the PMUT chip 804 may be configured to operate at a single resonant frequency. In some implementations, the array of PMUTs in the PMUT chip 804 may be configured to operate at different resonant frequencies. In some examples, the array of PMUTs may be configured to operate at resonant frequencies between 1 MHz and 80 MHz, between 1 MHz and 60 MHz, between 1 MHz and 40 MHZ, or between 10 MHz and 20 MHz. Operating at multiple different resonant frequencies can increase the bandwidth of the photoacoustic apparatus 800.

The PMUT chip 804 may include a piezoelectric layer sandwiched between a top electrode and a bottom electrode disposed over a passive layer and a supporting silicon substrate. In some implementations, the piezoelectric layer is selected from a group consisting of: aluminum nitride, aluminum scandium nitride, lead zirconate titanate, lithium niobate, zinc oxide, and co-polymer such as PVDF. In some implementations, the PMUT chip 804 may include a bimorph PMUT design. In some implementations, the PMUT chip 804 may include a pre-curved or self-curved PMUT design. In some implementations, a cavity side of the PMUT chip 804 may be oriented to be facing the blood vessel 860. In some implementations, the PMUT chip 804 may be transparent to the light 880 emitted by the EEL chip 808. In such cases, the PMUT chip 804 may even be arranged over the EEL chip 808, over the one or more light guides 830, or over the one or more diffraction gratings 850 on the substrate 820.

In some implementations, the PMUT chip 804 may be replaced with another micromachined ultrasonic transducer element such as a CMUT chip. By principle, CMUTs utilize a parallel plate capacitor that includes at least two electrodes and employ a high bias voltage.

The photoacoustic waves 870 detected by the PMUT chip 804 are converted into electrical charges in the form of ultrasonic receiver signals or ultrasonic data. The ASIC chip 806 is configured to receive ultrasonic receiver signals from the PMUT chip 804. In some implementations, the ASIC chip 806 processes the ultrasonic receiver signals, amplifies the ultrasonic receiver signals, produces a beamformed ultrasonic receiver image from the ultrasonic receiver signals, and detects the blood vessel 860 based at least in part on the beamformed ultrasonic receiver image. In some implementations, the ASIC chip 806 processes the ultrasonic receiver signals to allow for detection of arterial parameters such as, for example, size, diameter, area, etc. with respect to time periods that include distension and straining of the blood vessel 860. The ultrasonic receiver signals can be used to obtain information of blood flow/distension along a length of the blood vessel 860, thereby allowing for calculating of a pulse wave velocity. In some implementations, the ASIC chip 806 processes the ultrasonic receiver signals, produces a beamformed ultrasonic receiver image from the ultrasonic receiver signals, and estimates one or more blood vessel features based at least in part on the beamformed ultrasonic receiver image. The one or more blood vessel features may include blood vessel diameter, blood vessel area, blood vessel profile, blood vessel distension, volumetric flow, pulse wave velocity, blood vessel wall thickness, or combinations thereof.

In alternative implementations to having a separate PMUT chip 704 and VCSEL chip 708, a single integrated chip may include a plurality of PMUTs and a plurality of VCSELs. Rather than having separate chips for a receiver system and a light source system, a single integrated chip can perform both receiver and transmitter functions. Integration of receiver and transmitter functions in a single integrated chip can further enhance uniformity of illumination. In addition, this can provide increased integration and further miniaturization.

Figure 9:
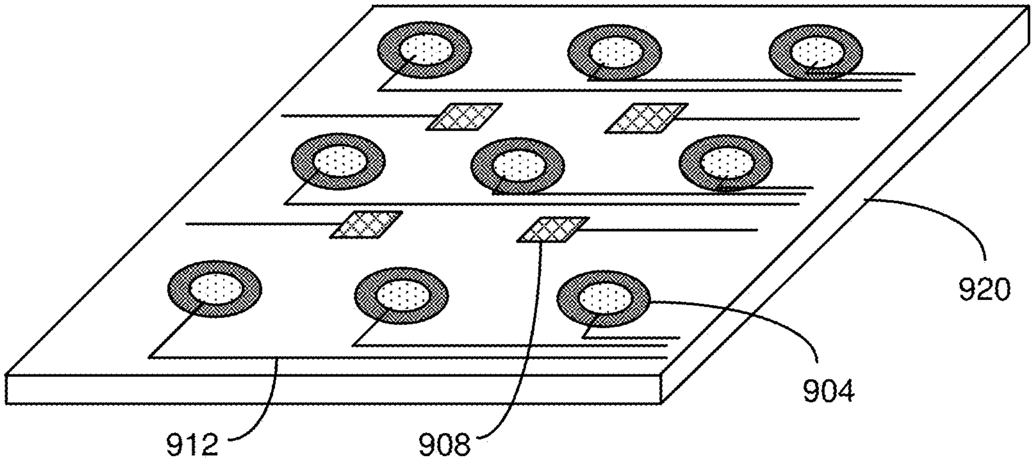
FIG. 9 shows an isometric view of a schematic illustration of an integrated chip including receiver elements and light-emitting elements.

FIG. 9 shows an isometric view of a schematic illustration of an integrated chip including receiver elements and light-emitting elements. An integrated chip 920 includes a plurality of receiver elements 904 and a plurality of light-emitting elements 908. The plurality of receiver elements 904 may include an array of ultrasonic transducer elements such as PMUTs or CMUTs. The plurality of receiver elements 904 may be interleaved between the plurality of light-emitting elements 908. The plurality of light-emitting elements 908 may include an array of laser diodes such as VCSELs or EELs.

The plurality of receiver elements 904 and the plurality of light-emitting elements 908 may be fabricated on the same integrated chip 920. This allows for uniform light illumination around the plurality of receiver elements 904. Each of the receiver elements 904 and each of the light-emitting elements 908 may have their own routing lines 912. This provides independently controllable receiver elements 904 and light-emitting elements 908. With the integrated chip 920, monolithic integration with an ASIC chip (not shown) is possible. In some implementations, the integrated chip 920 having receiver elements 904 and light-emitting elements 908 may be integrated with an ASIC chip by flip-chip bonding or eutectic bonding.

The integrated chip 920 having receiver elements 904 and light-emitting elements 908 may replace chips shown in the photoacoustic apparatuses of FIGS. 5, 7, and 8. That way, a separate chip for a receiver system and a separate chip for a light source system is not necessary. Specifically, the integrated chip 920 having receiver elements 904 and light-emitting elements 908 may be incorporated in the photoacoustic apparatus 500 of FIG. 5 by replacing the ultrasonic receiver system 504 and the in-plane light source system 508, incorporated in the photoacoustic apparatus 700 of FIG. 7 by replacing the PMUT chip 704 and the VCSEL chip 708, or incorporated in the photoacoustic apparatus 800 of FIG. 8 by replacing the PMUT chip 804 and the EEL chip 808.

Figure 10:
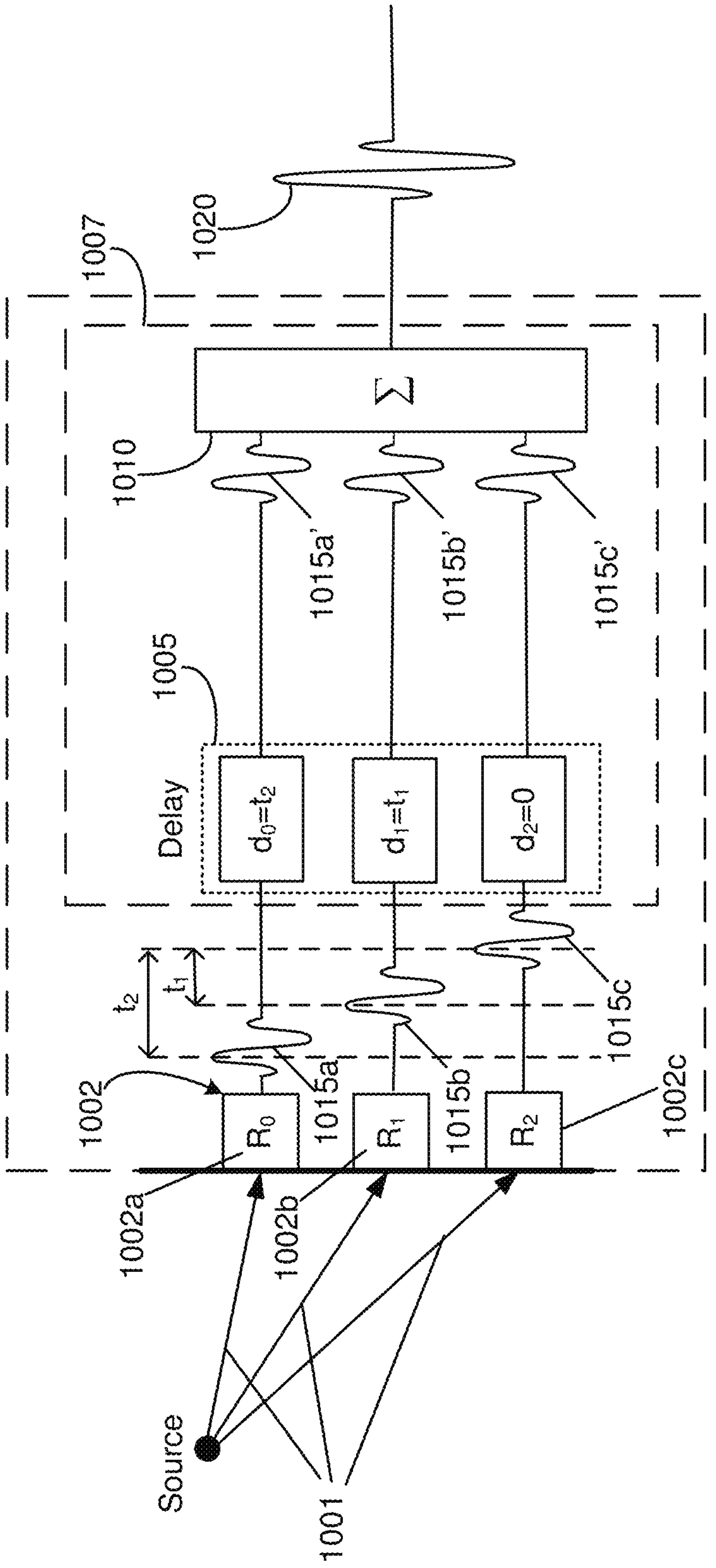
FIG. 10 shows an example photoacoustic apparatus that produces a beamformed ultrasonic receiver image according to some implementations.

FIG. 10 shows an example photoacoustic apparatus (such as any of the photoacoustic apparatuses described above) that produces a beamformed ultrasonic receiver image according to some implementations. According to some examples, the control system 1007 may be configured to detect a blood vessel within a target object based, at least in part, on the beamformed ultrasonic receiver image. In some such examples, the control system 1007 may be configured to estimate one or more blood vessel features based, at least in part, on the beamformed ultrasonic receiver image. In some examples, the control system 1007 may be configured to estimate one or more cardiac features based, at least in part, on one or more arterial signals, on the blood vessel features. According to some examples, the cardiac features may be, or may include, blood pressure.

In this example, the receiver-side beamforming process is a delay-and-sum beamforming process. As with other disclosed examples, the types, numbers, sizes and arrangements of elements shown in FIG. 10 and described herein, as well as the associated described methods, are merely examples.

In this example, a source is shown emitting ultrasonic waves 1001, which are detected by active ultrasonic receiver elements **1002*a*, 1002*b*, and 1002*c* of an array of ultrasonic receiver elements 1002. The array of ultrasonic receiver elements 1002*a*, 1002*b*, and 1002*c* is part of an ultrasonic receiver system 1002, examples of which are shown in FIGS. 5-8. The ultrasonic waves 1001 may, in some examples, correspond to the photoacoustic response of a target object to light emitted by a light source system of the photoacoustic apparatus. In this example, the active ultrasonic receiver elements 1002*a*, 1002*b*, and 1002*c* provide ultrasonic receiver signals 1015*a*, 1015*b* and 1015*c*, respectively, to the control system 1007**.

According to this example, the control system 1007 includes a delay module 1005 and a summation module 1010. In this example, the delay module 1005 is configured to determine whether a delay should be applied to each of the ultrasonic receiver signals **1015*a*, 1015*b* and 1015*c*, and if so, what delay will be applied. According to this example, the delay module 1005 determines that a delay $d_0$ of $t_2$ should be applied to the ultrasonic receiver signal 1015*a*, that a delay $d_1$ of $t_1$ should be applied to the ultrasonic receiver signal 1015*b* and that no delay should be applied to the ultrasonic receiver signal 1015*c*. Accordingly, the delay module 1005 applies a delay of $t_2$ to the ultrasonic receiver signal 1015*a*, producing the ultrasonic receiver signal 1015*a*', and applies a delay of $t_1$ to the ultrasonic receiver signal 1015*b*, producing the ultrasonic receiver signal 1015*b*'**.

In some examples, the delay module 1005 may determine what delay, if any, to apply to an ultrasonic receiver signal by performing a correlation operation on input ultrasonic receiver signals. For example, the delay module 1005 may perform a correlation operation on the ultrasonic receiver signals 1015_a_ and 1015_c_, and may determine that by applying a time shift of $t_2$ to the ultrasonic receiver signal 1015_a_, the ultrasonic receiver signal 1015_a_ would be strongly correlated with the ultrasonic receiver signal 1015_c_. Similarly, the delay module 1005 may perform a correlation operation on the ultrasonic receiver signals 1015_b_ and 1015_c_, and may determine that by applying a time shift of $t_1$ to the ultrasonic receiver signal 1015_b_, the ultrasonic receiver signal 1015_b_ would be strongly correlated with the ultrasonic receiver signal 1015_c_.

According to this example, the summation module 1010 is configured to sum the ultrasonic receiver signals 1015_a_', 1015_b_' and 1015_c_', producing the summed signal 1020. One may observe that the amplitude of the summed signal 1020 is greater than the amplitude of any one of the ultrasonic receiver signals 1015_a_, 1015_b_ or 1015_c_. In some instances, the signal-to-noise ratio (SNR) of the summed signal 1020 may be greater than the SNR of any of the ultrasonic receiver signals 1015_a_, 1015_b_ or 1015_c_.

Figure 11:
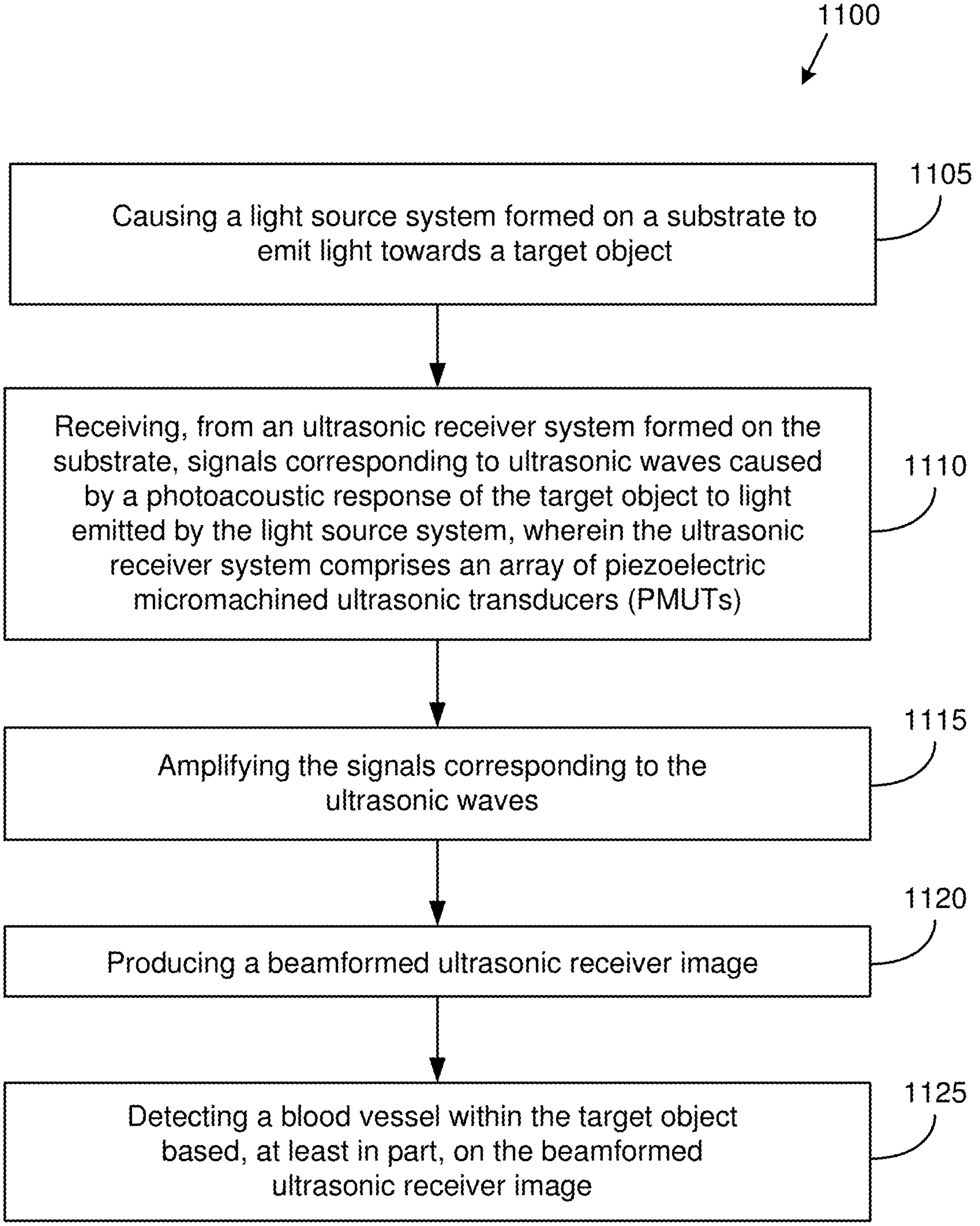
FIG. 11 shows a flow diagram of an example method of detecting a blood vessel according to some implementations.

FIG. 11 shows a flow diagram of an example method of detecting a blood vessel according to some implementations. The operations of a process 1100 may be performed in different orders and/or with different, fewer, or additional operations. One or more operations of the process 1100 may be performed using a photoacoustic apparatus described in any one of FIGS. 5, 7, 8, 12A-12B, and 13A-13B. In some implementations, the operations of the process 1100 may be implemented, at least in part, according to software stored in one or more non-transitory computer readable media. In some examples, some or all of the operations of the process 1100 may be performed by a control system such as a control system 507, ASIC chip 706, ASIC chip 806, or control system 1007.

In this example, block 1105 involves causing a light source system formed on a substrate to emit light towards a target object. The light source system may include one or more light-emitting chips such as one or more VCSEL chips or one or more EEL chips. The light may be propagated through an encapsulation layer that is transparent or substantially transparent to the light. The target object may include human skin that is in contact with a platen or the encapsulation layer of the photoacoustic apparatus. The light may cause illumination of one or more blood vessels in the target object.

Block 1110 involves receiving signals corresponding to ultrasonic waves caused by a photoacoustic response of the target object to light emitted by the light source system. The signals are received from an ultrasonic receiver system formed on the substrate. The ultrasonic receiver system includes an array of PMUTs. In some implementations, however, the array of PMUTs may be replaced by an array of CMUTs. In some implementations, the array of PMUTs or CMUTs may be integrated with an array of light-emitting elements in an integrated receiver/transmitter chip. The array of PMUTs or CMUTs are formed on the same substrate or chip as the light source system. The ultrasonic receiver system may convert the ultrasonic waves into electrical charges that correspond to the signals.

Block 1115 involves amplifying the signals corresponding to the ultrasonic waves. In image processing, the signals received from the ultrasonic receiver system may pass through, among other things, amplifiers, analog or digital mixers or multipliers, switches, analog digital converter, passive filters, active analog filters, etc.

Block 1120 involves producing a beamformed ultrasonic receiver image. The large array of PMUTs or CMUTs in the ultrasonic receiver system may provide better beam formation for improved image quality. Algorithms associated with time delay and summation are applied to the signals received from the ultrasonic receiver system. Construction of the beamformed ultrasonic receiver image occurs based at least in part on the signals received from the ultrasonic receiver system.

Block 1125 involves detecting a blood vessel within the target object based, at least in part, on the beamformed ultrasonic receiver image. The blood vessel may, for example, be detected according to a time window that corresponds with the speed of sound traversing an expected range of depth to a blood vessel. Alternatively, or additionally, the blood vessel may be detected according to one or more characteristics of the photoacoustic responses of the blood vessel walls, of blood within the blood vessel, or a combination thereof. In some examples, determining the selected area may involve estimating a signal-to-noise ratio (SNR) of ultrasonic receiver signals corresponding to at least a portion of the blood vessel and selecting an area corresponding to a highest SNR. In some implementations, the beamformed ultrasonic receiver image is used to assist in estimating one or more blood vessel features. For instance, the one or more blood vessel features may include blood vessel diameter, blood vessel area, blood vessel profile, blood vessel distension, volumetric flow, pulse wave velocity, blood vessel wall thickness, or combinations thereof. In some implementations, the process 1100 may further include estimating one or more cardiac or arterial features based, at least in part, on the detected blood vessel. For example, the cardiac or arterial feature may include blood pressure. Other cardiac or arterial features may include diameter, distention, and heart rate waveform, among other cardiac or arterial features.

Various artifact signals such as electromagnetic interference (EMI) signals, signals from reflected light, and signals from reflected acoustic waves, may adversely impact the performance of a PAPG device. In other words, the SNR performance of the PAPG device is adversely impacted by EMI, unless EMI is mitigated. However, utilization of an array of PMUTs in the present disclosure lowers capacitance to reduce cross-talk, EMI, and light source coupling. To further limit the effects of artifact signals such as EMI, a shielding system may be incorporated in the PAPG device of the present disclosure.

Figure 12A:
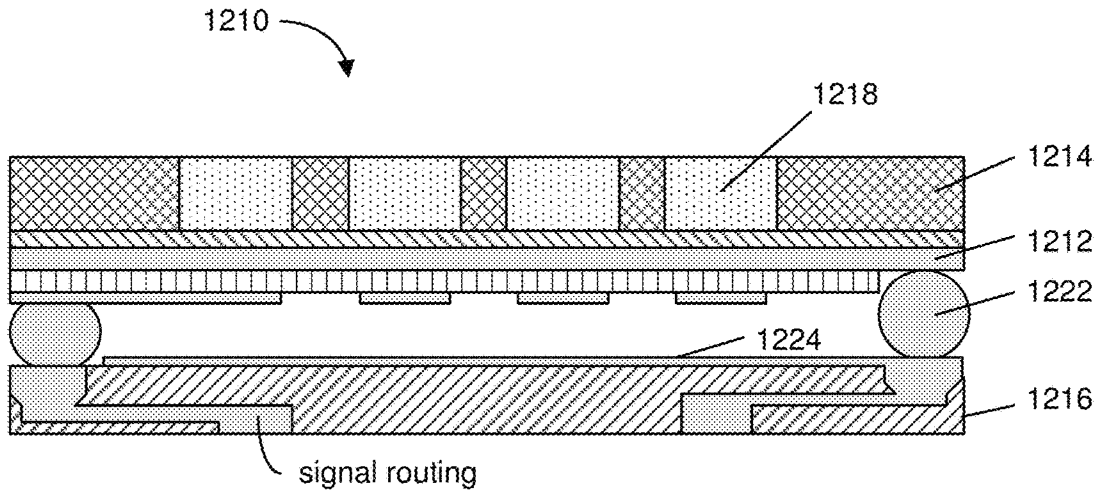
FIG. 12A shows a cross-sectional schematic illustration of a PAPG device that includes a shielding layer.

FIG. 12A shows a cross-sectional schematic illustration of a PAPG device 1210 that includes a shielding layer 1212. The shielding layer 1212 is positioned between a PMUT chip 1214 and a PCB 1216. The PMUT chip 1214 can include an array of PMUTs. In FIG. 12A, the PMUT chip 1214 may be inverted, where cavities in the array of PMUTs may be filled with an electrical insulating material 1218 that serves as a tissue-coupling medium with human tissue. In some cases, the electrical insulating material 1218 may include PDMS or parylene. The electrical insulating material 1218 may encapsulate the PMUT chip 1214 while providing mechanical protection for thin membranes and electrical insulation for electrodes. PAPG devices may be packaged using any suitable technique, such as flip-chip bonding or wire bonding. In FIG. 12A, the PAPG device 1210 is packaged by flip-chip bonding using, for example, solder balls 1222 to provide electrical interconnection between the PCB 1216 and the PMUT chip 1214.

The shielding layer 1212 may be integrated in a surface micromachined process. The shielding layer 1212 may function to prevent EMI coupling into faint photoacoustic signals. In some implementations, the shielding layer 1212 may additionally or alternatively function as a mirror to prevent any reflected/scattered light from a light source system (not shown) in the PAPG device 1210 that would otherwise produce a photoacoustic signal on the piezoelectric layer of the PMUT chip 1214. In some implementations, the PAPG device 1210 of FIG. 12A may further include a shielding plane 1224 for additional shielding. The shielding plane 1224 may be positioned on the PCB 1216, where the shielding plane 1224 may be completed using a ground plane of the PCB 1216.

Figure 12B:
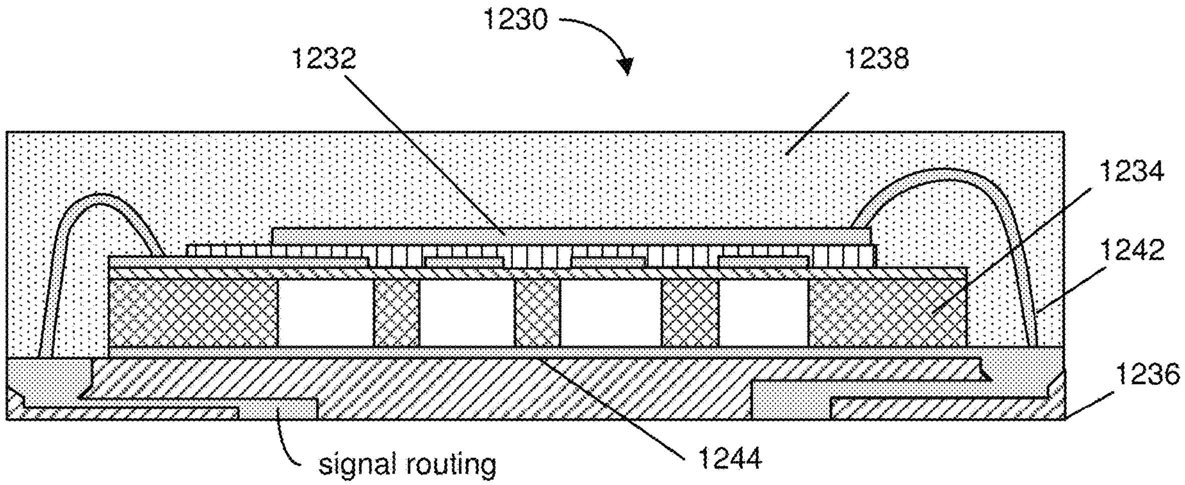
FIG. 12B shows a cross-sectional schematic illustration of an alternative PAPG device that includes a shielding layer.

FIG. 12B shows a cross-sectional schematic illustration of a PAPG device 1230 that includes a shielding layer 1232. The shielding layer 1232 is positioned on and over a PMUT chip 1234, and an electrical insulating material 1238 is positioned on and over the shielding layer 1232. The PMUT chip 1234 is formed on and over a PCB 1236. The PMUT chip 1234 can include an array of PMUTs. The electrical insulating material 1238 serves as a tissue-coupling medium with human tissue. In some cases, the electrical insulating material 1238 may include PDMS or parylene. The electrical insulating material 1238 may encapsulate the PMUT chip 1234 and shielding layer 1232 while providing mechanical protection for thin membranes and electrical insulation for electrodes. In FIG. 12B, the PAPG device 1230 is packaged by wire bonding using wires 1242, and particularly by wire bonding the PMUT chip 1234 onto the PCB 1236 with the wires 1242.

The shielding layer 1232 may be integrated in a surface micromachined process. The shielding layer 1232 may function to prevent EMI coupling into faint photoacoustic signals. In some implementations, the shielding layer 1232 may additionally or alternatively function as a mirror to prevent any reflected/scattered light from a light source system (not shown) in the PAPG device 1230 that would otherwise produce a photoacoustic signal on the piezoelectric layer of the PMUT chip 1234. In some implementations, the PAPG device 1230 of FIG. 12B may further include a shielding plane 1244 for additional shielding. The shielding plane 1244 may be positioned on the PCB 1236, where the shielding plane 1244 may be completed using a ground plane of the PCB 1236.

The PAPG device of the present disclosure may be formed on flexible printed circuits that can be easily integrated in compact devices such as wristwatches and wristbands. Ultrasonic receiver systems such as one or more PMUT chips may be formed on a flexible PCB. In addition, light source systems such as one or more VCSEL chips or one or more EEL chips may be formed on the flexible PCB. A gap may be provided between the ultrasonic receiver system and the light source system to allow for flexibility and conformability to a wrist shape. The thin form factor of the PAPG device of the present disclosure allows seamless integration into a strap for a wristwatch or wristband without having to integrate a thick module. Integration with a flexible PCB also provides flexibility in a location of the PAPG device. Signal trace shielding can be incorporated in the flexible PCB using ground layers within the flexible PCB.

Figure 13A:
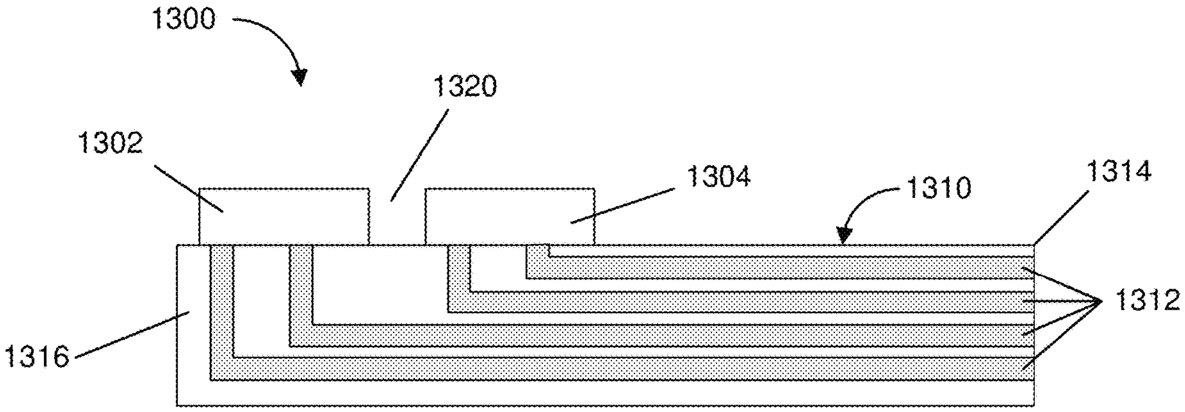
FIG. 13A shows a cross-sectional schematic illustration of a PAPG device on a flexible printed circuit.

FIG. 13A shows a cross-sectional schematic illustration of a PAPG device 1300 on a flexible printed circuit 1310. The PAPG device 1300 includes a PMUT chip 1302 on the flexible printed circuit 1310. The PMUT chip 1302 serves as an ultrasonic receiver system and may include an array of PMUTs. The PAPG device 1300 further includes a light source system such as a VCSEL chip 1304 on the flexible printed circuit 1310. A gap 1320 may be provided between the PMUT chip 1302 and the VCSEL chip 1304 to afford flexibility and conformability to a wrist shape. The flexible printed circuit 1310 may include a plurality of signal traces 1312 for routing electrical signals to and from the PMUT chip 1302, and routing electrical signals to and from the VCSEL chip 1304. The electrical signals may cause unwanted cross-talk and electromagnetic interference (EMI). Ground layers 1314 in the flexible printed circuit 1310 may function as shielding to mitigate the effects of cross-talk and EMI from the signal traces 1312. The flexible printed circuit 1310 may further include electrical insulation 1316 to provide electrical insulation between electrodes.

Figure 13B:
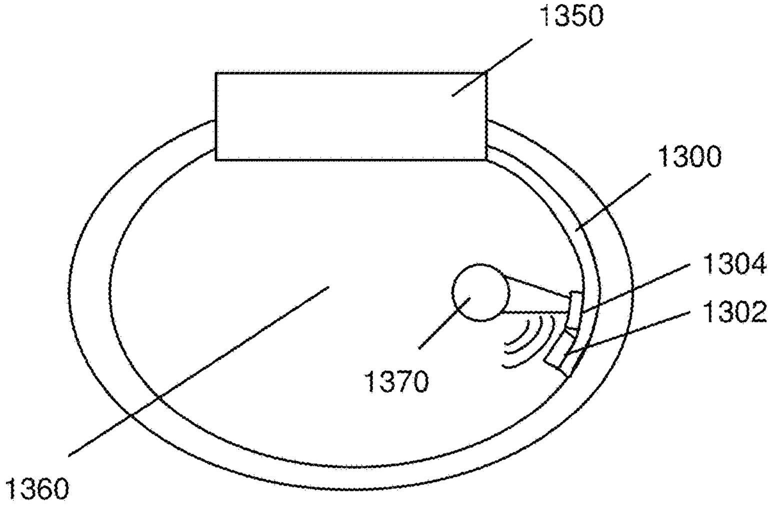
FIG. 13B shows a cross-sectional schematic illustration of the PAPG device integrated in a wearable apparatus such as a flexible watch.

FIG. 13B shows a cross-sectional schematic illustration of the PAPG device 1300 integrated in a wearable apparatus such as a flexible watch 1350. The flexible watch 1350 may be worn around a wrist 1360. The PAPG device 1300 uses photoacoustic imaging to identify one or more blood vessels such as an artery 1370 in the wrist 1360. The PAPG device 1300 may be located on interior surfaces of the flexible watch 1350 facing towards the wrist 1360, where the location of the PAPG device 1300 is flexible along the flexible watch 1350.

Implementation examples are described in the following numbered clauses:

1. An apparatus, including: a substrate; a light source system formed on the substrate and configured to provide light to a target object; an ultrasonic receiver system formed on the substrate and including an array of ultrasonic transducer elements, where the ultrasonic receiver system is configured to detect acoustic waves corresponding to a photoacoustic response of the target object to light provided by the light source system; and an encapsulation layer disposed over the array of ultrasonic transducer elements and the light source system, where the encapsulation layer is transparent to the light provided by the light source system.

2. The apparatus of clause 1, where the array of ultrasonic transducer elements includes an array of piezoelectric micromachined ultrasonic transducers (PMUTs).

3. The apparatus of clause 2, where the array of PMUTs are configured to operate at different resonant frequencies.

4. The apparatus of clause 2 or clause 3, where each of the PMUTs includes a piezoelectric layer sandwiched between a top electrode and a bottom electrode disposed on a supporting silicon substrate, wherein a material of the piezoelectric layer is selected from a group consisting of: aluminum nitride (AlN), aluminum scandium nitride (AlScN), lead zirconate titanate (PZT), lithium niobate, zinc oxide, and co-polymer.

5. The apparatus of any one of clauses 2-4, where the array of PMUTs are transparent to the light provided by the light source system.

6. The apparatus of any one of clauses 2-5, where the light source system and the ultrasonic receiver system are integrated in an integrated receiver/transmitter chip, and the array of PMUTs is interleaved between a plurality of light-emitting elements in the light source system.

7. The apparatus of clause 1, where the array of ultrasonic transducer elements comprises an array of capacitive micromachined ultrasonic transducers (CMUTs).

8. The apparatus of any one of clauses 1-7, further including a control system formed on the substrate, wherein the control system comprises one or more processors and one or more memory devices, wherein the control system is in electrical communication with the ultrasonic receiver system and the light source system.

9. The apparatus of clause 8, where the substrate comprises a printed circuit board or flexible circuit board on which each of the light source system, ultrasonic receiver system, and control system is formed.

10. The apparatus of clause 8 or clause 9, where the control system is configured with instructions to perform the following operations: process ultrasonic receiver signals from the ultrasonic receiver system; amplify the ultrasonic receiver signals; produce a beamformed ultrasonic receiver image; and detect a blood vessel within the target object based at least in part on the beamformed ultrasonic receiver image.

11. The apparatus of clause 10, where the control system is further configured with instructions to perform the following operation: estimate one or more cardiac features based, at least in part, on the blood vessel within the target object.

12. The apparatus of any one of clauses 1-11, where a thickness of the apparatus comprising the encapsulation layer, the substrate, the ultrasonic receiver system, and the light source system is equal to or less than about 4 mm.

13. The apparatus of any one of clauses 1-12, where the light source system includes one or more vertical cavity surface emitting laser (VCSEL) chips.

14. The apparatus of any one of clauses 1-13, where the light source system comprises one or more edge-emitting laser (EEL) chips.

15. The apparatus of clause 14, further including: a plurality of light guides to route light from the one or more EEL chips to multiple areas located on a plane of the substrate, and a plurality of diffraction gratings optically coupled to the plurality of light guides and configured to direct light from each of the multiple areas to the target object.

16. The apparatus of any one of clauses 1-15, where an acoustic impedance of the encapsulation layer matches or substantially matches an acoustic impedance of human skin.

17. An apparatus for estimating one or more cardiac features, the apparatus including: a substrate; a light source system including a plurality of light-emitting elements formed on the substrate; an ultrasonic receiver system including an array of piezoelectric micromachined ultrasonic transducers (PMUTs) formed on the substrate; a control system formed on the substrate; an encapsulation layer disposed over the plurality of light-emitting elements, the array of PMUTs, and the control system; where the control system is configured with instructions to perform the following operations: cause the light source system to emit light towards human tissue in contact with an outer surface of the encapsulation layer; receive ultrasonic signals from each of the PMUTs in the ultrasonic receiver system corresponding to ultrasonic waves generated by the human tissue; identify one or more blood vessels; and estimate one or more cardiac features based, at least in part, on the one or more blood vessels.

18. The apparatus of clause 17, where the control system is further configured with instructions for performing the following operations: amplify the ultrasonic signals received from each of the PMUTs, and produce a beamformed ultrasonic receiver image, where the one or more blood vessels are identified based, at least in part, on the beamformed ultrasonic receiver image.

19. The apparatus of clause 17 or clause 18, where the array of PMUTs is configured to operate at different resonant frequencies.

20. The apparatus of any one of clauses 17-19, where the encapsulation layer is transparent to the light emitted by the light source system.

21. The apparatus of any one of clauses 17-20, where a thickness of the apparatus is equal to or less than about 4 mm.

22. A method of detecting a blood vessel, the method including: causing a light source system formed on a substrate to emit light towards a target object; receiving, from an ultrasonic receiver system formed on the substrate, signals corresponding to ultrasonic waves caused by a photoacoustic response of the target object to light emitted by the light source system, where the ultrasonic receiver system comprises an array of piezoelectric micromachined ultrasonic transducers (PMUTs); amplifying the signals corresponding to the ultrasonic waves; producing a beamformed ultrasonic receiver image; and detecting a blood vessel within the target object based, at least in part on the beamformed ultrasonic receiver image.

23. The method of clause 22, further including: estimating one or more cardiac features based, at least in part, on the beamformed ultrasonic receiver image.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word “exemplary” is used exclusively herein, if at all, to mean “serving as an example, instance, or illustration.” Any implementation described herein as “exemplary” is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:

1. An apparatus, comprising:

a substrate comprising a printed circuit board, a flexible circuit board, or a combination thereof;

a light source system comprising one or more light-emitting chips mounted on a major surface of the substrate and configured to provide light to a target object;

an ultrasonic receiver system formed on the major surface of the substrate and comprising an array of piezoelectric micromachined ultrasonic transducers (PMUTs), wherein the array of PMUTs are configured to operate at different resonant frequencies, wherein the ultrasonic receiver system is configured to detect acoustic waves corresponding to a photoacoustic response of the target object to light provided by the light source system; and an encapsulation layer disposed over the array of ultrasonic transducer elements and the light source system so that the array of ultrasonic transducer elements and the light source system are enclosed within a material of the encapsulation layer, wherein the encapsulation layer is transparent to the light provided by the light source system, wherein a thickness of the apparatus comprising the encapsulation layer, the substrate, the ultrasonic receiver system, and the light source system is equal to or less than 4 mm.

2. The apparatus of claim 1, wherein each of the PMUTs comprises a piezoelectric layer sandwiched between a top electrode and a bottom electrode disposed on a supporting silicon substrate, wherein a material of the piezoelectric layer is selected from a group consisting of: aluminum nitride (AlN), aluminum scandium nitride (AlScN), lead zirconate titanate (PZT), lithium niobate, zinc oxide, and co-polymer.

3. The apparatus of claim 1, wherein the array of PMUTs are transparent to the light provided by the light source system.

4. The apparatus of claim 1, wherein the light source system and the ultrasonic receiver system are integrated in an integrated receiver/transmitter chip, wherein the array of PMUTs is interleaved between a plurality of light-emitting elements in the light source system.

5. The apparatus of claim 1, wherein the light source system comprises one or more vertical cavity surface emitting laser (VCSEL) chips.

6. The apparatus of claim 1, wherein an acoustic impedance of the encapsulation layer matches or substantially matches an acoustic impedance of human skin.

7. The apparatus of claim 1, further comprising:

a control system formed on the major surface of the substrate, wherein the control system comprises one or more processors and one or more memory devices, wherein the control system is in electrical communication with the ultrasonic receiver system and the light source system, wherein the light source system, the ultrasonic receiver system, and the control system are formed on the printed circuit board, the flexible circuit board, or the combination thereof.

8. The apparatus of claim 7, wherein the control system is configured with instructions to perform the following operations:

process ultrasonic receiver signals from the ultrasonic receiver system;

amplify the ultrasonic receiver signals;

produce a beamformed ultrasonic receiver image; and detect a blood vessel within the target object based at least in part on the beamformed ultrasonic receiver image.

9. The apparatus of claim 8, wherein the control system is further configured with instructions to perform the following operation:

estimate one or more cardiac features based, at least in part, on the blood vessel within the target object.

10. The apparatus of claim 1, wherein the light source system comprises one or more edge-emitting laser (EEL) chips.

11. The apparatus of claim 10, further comprising:

a plurality of light guides to route light from the one or more EEL chips to multiple areas located on a plane of the substrate; and a plurality of diffraction gratings optically coupled to the plurality of light guides and configured to direct light from each of the multiple areas to the target object.

12. An apparatus for estimating one or more cardiac features, the apparatus comprising:

a substrate comprising a printed circuit board, a flexible circuit board, or a combination thereof;

a light source system comprising a plurality of light-emitting elements mounted on a major surface of the substrate;

an ultrasonic receiver system comprising an array of piezoelectric micromachined ultrasonic transducers (PMUTs) formed on the major surface of the substrate, wherein the array of PMUTs is configured to operate at different resonant frequencies;

a control system formed on the major surface of the substrate; and an encapsulation layer disposed over the plurality of light-emitting elements, the array of PMUTs, and the control system so that the plurality of light-emitting elements, the array of PMUTs, and the control system are enclosed within a material of the encapsulation layer, wherein a thickness of the apparatus is equal to or less than 4 mm;

wherein the control system is configured with instructions to perform the following operations:

cause the light source system to emit light towards human tissue in contact with an outer surface of the encapsulation layer;

receive ultrasonic signals from each of the PMUTs in the ultrasonic receiver system corresponding to ultrasonic waves generated by the human tissue;

identify one or more blood vessels; and estimate one or more cardiac features based, at least in part, on the one or more blood vessels.

13. The apparatus of claim 12, wherein the control system is further configured with instructions for performing the following operations:

amplify the ultrasonic signals received from each of the PMUTs; and produce a beamformed ultrasonic receiver image, wherein the one or more blood vessels are identified based, at least in part, on the beamformed ultrasonic receiver image.

14. The apparatus of claim 12, wherein the encapsulation layer is transparent to the light emitted by the light source system.

15. A method of detecting a blood vessel, the method comprising:

causing a light source system comprising one or more light-emitting chips mounted on a major surface of a substrate to emit light towards a target object, wherein the substrate comprises a printed circuit board, a flexible circuit board, or a combination thereof;

receiving, from an ultrasonic receiver system formed on the major surface of the substrate, signals corresponding to ultrasonic waves caused by a photoacoustic response of the target object to light emitted by the light source system, wherein the ultrasonic receiver system comprises an array of piezoelectric micromachined ultrasonic transducers (PMUTs), wherein the array of PMUTs is configured to operate at different resonant frequencies, wherein the ultrasonic receiver system and the light source system are enclosed within a material of an encapsulation layer;

amplifying the signals corresponding to the ultrasonic waves;

producing a beamformed ultrasonic receiver image; and detecting a blood vessel within the target object based, at least in part on the beamformed ultrasonic receiver image, wherein a thickness of an apparatus performing the method comprising the encapsulation layer, the substrate, the ultrasonic receiver system, and the light source system is equal to or less than 4 mm.

16. The method of claim 15, further comprising:

estimating one or more cardiac features based, at least in part, on the beamformed ultrasonic receiver image.

* * * * *